(12) United States Patent
Bartis et al.

(10) Patent No.: US 7,790,765 B2
(45) Date of Patent: Sep. 7, 2010

(54) HYDROXY SULFONATE OF QUINONE COMPOUNDS AND THEIR USES

(75) Inventors: Judit Bartis, Westford, MA (US); Erika Volckova, Concord, MA (US); Manish Tandon, Framingham, MA (US); Deirdre Lowe, Salem, MA (US); Martin P. Redmon, Oxford, MA (US)

(73) Assignee: ArQule, Inc., Woburn, MA (US)

( * ) Notice: Subject to any disclaimer, the term of this patent is extended or adjusted under 35 U.S.C. 154(b) by 233 days.

(21) Appl. No.: 12/150,914

(22) Filed: Apr. 30, 2008

(65) Prior Publication Data

US 2009/0028952 A1    Jan. 29, 2009

Related U.S. Application Data

(60) Provisional application No. 60/914,971, filed on Apr. 30, 2007.

(51) Int. Cl.
  A61K 31/35    (2006.01)
  C07D 311/92   (2006.01)
(52) U.S. Cl. .................. 514/454; 424/499; 549/389
(58) Field of Classification Search .......... 549/389; 514/454
  See application file for complete search history.

(56) References Cited

U.S. PATENT DOCUMENTS

| | | | | |
|---|---|---|---|---|
| 4,963,565 | A | 10/1990 | Gangadharam | 514/311 |
| 5,120,843 | A | 6/1992 | McCall et al. | 544/123 |
| 5,210,239 | A | 5/1993 | Abe et al. | 552/307 |
| 5,385,942 | A | 1/1995 | Abe et al. | 514/568 |
| 5,534,536 | A | 7/1996 | Ohuchida et al. | |
| 5,674,900 | A | 10/1997 | Ubilas et al. | 514/557 |
| 5,763,625 | A | 6/1998 | Boothman et al. | 549/390 |
| 5,780,514 | A | 7/1998 | Gutteridge et al. | 514/682 |
| 5,783,598 | A | 7/1998 | Boyd et al. | 514/454 |
| 5,824,700 | A | 10/1998 | Frydman et al. | 514/454 |
| 5,840,900 | A | 11/1998 | Greenwald et al. | |
| 5,880,131 | A | 3/1999 | Greenwald et al. | |
| 5,969,163 | A | 10/1999 | Frydman et al. | 549/389 |
| 5,977,163 | A | 11/1999 | Li et al. | |
| 6,245,807 | B1 | 6/2001 | Pardee et al. | 514/454 |
| 6,376,470 | B1 | 4/2002 | Greenwald et al. | |
| 6,458,974 | B1 | 10/2002 | Jiang et al. | 549/389 |
| 6,608,076 | B1 | 8/2003 | Greenwald et al. | |
| 6,962,944 | B2 | 11/2005 | Jiang et al. | 514/454 |
| 7,074,824 | B2 | 7/2006 | Jiang et al. | 514/455 |
| 2002/0169135 | A1 | 11/2002 | Pardee et al. | 514/27 |
| 2003/0091639 | A1 | 5/2003 | Jiang et al. | 424/486 |
| 2004/0071775 | A1 | 4/2004 | Jiang et al. | 424/486 |
| 2004/0087610 | A1 | 5/2004 | Pardee et al. | |
| 2004/0266857 | A1 | 12/2004 | Jiang et al. | 514/437 |
| 2006/0034796 | A1 | 2/2006 | Ashwell et al. | |
| 2006/0035963 | A1 | 2/2006 | Ashwell et al. | |

FOREIGN PATENT DOCUMENTS

| | | |
|---|---|---|
| EP | 0040506 A2 | 11/1981 |
| JP | 05124969 A | 5/1993 |
| WO | WO 94/04145 | 3/1994 |
| WO | WO-9505200 A1 | 2/1995 |
| WO | WO 96/33988 | 10/1996 |
| WO | WO-9741093 A1 | 11/1997 |
| WO | WO 00/61142 | 10/2000 |
| WO | WO-0066175 A2 | 11/2000 |
| WO | WO-0126693 A2 | 4/2001 |
| WO | WO-0170275 A2 | 9/2001 |
| WO | WO-02058694 A2 | 8/2002 |
| WO | WO 03/011224 A2 | 2/2003 |
| WO | WO-03053473 A2 | 7/2003 |
| WO | WO-03090710 A1 | 11/2003 |
| WO | WO 2004/006849 A2 | 1/2004 |
| WO | WO 2004/045557 A2 | 6/2004 |
| WO | WO-2005082356 A2 | 9/2005 |
| WO | WO-2005082357 A1 | 9/2005 |
| WO | WO 2006/020719 A2 | 2/2006 |
| WO | WO-2006020722 A2 | 2/2006 |
| WO | WO 2006/128120 A2 | 11/2006 |

OTHER PUBLICATIONS

Boorstein et al., "Coordinate Inhibition of DNA Synthesis and Thymidylate Synthase Activity Following DNA Damage and Repair", *Biochem. Biophys. Commun.*, 117(1):30-36 (1983).

Boothman et al., "Potentiation of Halogenated Pyrimidine Radiosensitizers in Human Carcinoma Cells by β-Lapachone (3,4-Dihydro-2,2-dimethyl-2H-naphto[1,2-b]pyran-5,6-dione), a Novel DNA Repair Inhibitor", *Cancer Res.*, 47:5361-5366 (1987).

Bradshaw et al., "Preclinical Evaluation of AminoAcid Prodrugs of Novel Antitumor 2-(4-Amino-3-Methylphenyl)Benzothiazoles", *Mol. Cancer Ther.*, 1(4):239-46 (2002).

Choe et al., "Anticancer Drug Delivery Systems: Multi-Loaded $N^4$-Acyl Poly(Ethylene Glycol) Prodrugs of Ara-C. II. Efficacy in Ascites and Solid Tumors", *J. Controlled Release*, 79:55-70 (2002).

Choe et al., "Anticancer Drug Delivery Systems: $N^4$-Acyl Poly(Ethyleneglycol) Prodrugs of Ara-C. I. Efficacy in Solid Tumors", *J. Controlled Release*, 79:41-53 (2002).

Conover et al., "Camptothecin Delivery Systems: Enhanced Efficacy and Tumor Accumulation of Camptothecin Following its Conjugation to Polyethylene Glycol via a Glycine Linker", *Cancer Chemother Pharmacol.*, 42(4):407-414 (1998).

Conover et al., "Camptothecin Delivery Systems: The Utility of Amino Acid Spacers for the Conjugation of Camptothecin with Polyethylene Glycol to Create Prodrugs", *Anticancer Drug Design*, 14(6):499-506 (1999).

(Continued)

*Primary Examiner*—Bernard Dentz
(74) *Attorney, Agent, or Firm*—Mintz Levin Cohn Ferris Glovsky and Popeo, P.C.; Ivor R. Elrifi; Matthew Pavao

(57) ABSTRACT

The present invention provides sodium 6-hydroxy-2,2-dimethyl-5-oxo-3,4,5,6-tetrahydro-2H-benzo(h)chromene-6-sulfonate, and its synthesis and uses in the treatment of cancer.

18 Claims, 4 Drawing Sheets

OTHER PUBLICATIONS

DiChenna et al., "Preparation and Cytotoxicity Toward Cancer Cells of Mono(arylimino) Derivatives of β-Lapachone", *J. Medicinal Chem.*, 44:2486-2489 (2001).

Driscoll et al., "Structure-Antitumor Activity Relationships Among Quinone Derivative", *Cancer Chemother. Reports Part 2*, 4(2):1-362 (1974).

Duncan, Ruth, "The Dawning Era of Polymer Therapeutics", *Nature Rev.*, 2:347-360 (2003).

Etrych et al., "New HPMA Copolymers Containing Doxorubicin Bound Via pH-Sensitive Linkage: Synthesis and Preliminary In Vitro and In Vivo Biological Properties", *J.Controlled Release*, 73:89-102 (2001).

Etrych et al., "Synthesis of HPMA Copolymers Containing Doxorubicin Bound via a Hydrazone Linkage. Effect of Spacer on Drug Release and In Vitro Cytotoxicity", *Macromolecular Bioscience*, 2(1):43-52 (2002).

Frydman et al., "Induction of DNA Topoisomerase II-Mediated DNA Cleavage by β-Lapachone and Related Naphthoquinones", *Cancer Res.*, 57:620-627 (1997).

Gehrhardt et al., "Soluble Polymers in Organic Chemistry 5. Preparation of Carboxyl- and Amino-Terminal Polyethylene Glycol of Low Molecular Weight", *Polymer Bull.*, 18:487-493 (1987).

Greenwald et al., "Camptothecin-20-PEG Ester Transport Forms: the Effect of Spacer Groups on Antitumor Activity", *Bioorganic & Medicinal Chemistry*, 6:551-562 (1998).

Greenwald et al., "Controlled Release of Proteins from Their Poly-(ethylene Glycol) Conjugates: Drug Delivery Systems Employing 1,6-Elimination", *Bioconj. Chem.*, 14(2):395-403 (2003).

Greenwald et al., "Drug Delivery System. 2. Camptothecin 20-*O*-Poly (Ethylene Glycol) Ester Transport Forms", *J. Med. Chem.*, 39(10):1938-1940 (1996).

Greenwald et al., "Drug Delivery Systems Based on Trimethyl Lock Lactonization: Poly(Ethylene Glycol) Prodrugs of Amino-Containing Compounds", *J. Med. Chem.*, 43(3):475-487 (2000).

Greenwald et al., "Drug Delivery Systems Employing 1,4- or 1,6-Elimination: Poly(Ethylene Glycol) Prodrugs of Amine-Containing Compounds", *J. Med. Chem*, 42(18):3657-3667 (1999).

Greenwald et al., "Drug Delivery Systems: Water Soluble Taxol 2'-Poly(ethylene glycol) Ester Prodrugs-Design and In Vivo Effectiveness", *J. Med. Chem.*, 39(2):424-431 (1996).

Greish et al., "Copoly(styrene-maleic acid)-Pirarubicin Micelles: High Tumor-Targeting Efficiency with Little Toxicity", *Bioconjugate Chem..*, 16(1):230-236 (2005).

Hooker, C., "The Constitution of Lapachol and its Derivatives. Part V. The Structure of Paterno's 'Isolapachone'", *J. Am. Chem. Soc.* 58(7):1190-1197 (1936).

Krishnan et al., "Novel Mechanisms of DNA Topoisomerase II Inhibition by Pyranonaphthoquinone Derivatives-Eleutherin, α Lapachone, and β Lapachone", *Biochem Pharm*, 60:1367-1379(2000).

Kumi-Diaka et al., "Potential Mechanism of Phytochemical-Induced Apoptosis in Human Prostate Adenocarcinoma Cells: Therapeutic Synergy in Genistein and β-Lapochone Combination Treatment", *Cancer Cell Treatment International*, 4:5 (2004).

Matsumura et al., "A New Concept for Macromolecular Therapeutics in Cancer Chemotherapy: Mechanism of Tumoritropic Accumulation of Proteins and an Antitumor Agent Smancs", *Cancer Res.*, 46(12 Pt 1):6387-6392(1986).

Ochoa et al., "A Phase I Study of PEG-Camptothecin (PEG-C1 Advanced Solid Tumors: A Novel Formulation f Active Agent", *Proc. Am. Soc. Clin. Oncology*, 19:(Abstract 770), (2000).

Ohya et al., "Synthesis and Cytotoxic Activity of Conjugates of Monomethoxy-Poly(ethylene glycol) End-capped with Doxorubicin via Ester, Amide, or Schiff's Base Bond", *Journal of Bioactive and Compatible Polymers*, 10:51-66 (1995).

Pawliszyn, J., "Sampling and Sample Preparation for Field and Laboratory", Elsevier, p. 618 (2002).

Pink et al., "NAD(P)H:Quinone Oxidoreductase Activity is the Principal Determinant of β-Lapachone Cytotoxicity", *J. Biol. Chem.*, 275(8):5416-5424 (2000).

Powis et al., "Molecular Pharmacology and Antitumor Activity of Palmarumycin-Based Inhibitors or Thioredoxin Reductase", *Molecular Cancer Therapeutics*, 5(3):630-636 (2006).

Reinicke et al., Development of β-Lapachone Prodrugs for Therapy Against Human Cancer Cells with Elevated NAD(P)H:Quinone Oxidoreductase I Levels, *Clin. Cancer Res.*, 11(8):3055-64 (2005).

Rowinsky et al., Phase I and Pharmacologic Study of High Doses of the Topoisomerase I Inhibitor Topotecan with Granulocyte Colony-Stimulating Factor in Patients with Solid Tumors, *Journal of Clinical Oncology*, 14(4):1224-1235 (1996).

Sartomer Webste printed on May 24, 2006 (4 pages).

Suggs et al., "Facile Hydrolysis and Formation of Amide Bonds by N-Hydroxyethylation of α-Amino Acids", *Tetrahedron Letters*, 38(13):2227-2230(1997).

Veronese et al., "Preparation, Physico-Chemical and Pharmacokinetic Characterization of Monomethyoxypoly(Ethylene Glycol)-Derivatized Superoxide Dismutase", *Journal of Controlled Release*, 10:145-154(1989).

Villar-Garea et al., "Procaine is a DNA-demethylating Agent with Growth-Inhibitory Effects in Human Cancer Cells", *Cancer Res.*, 63:4984-4989 2003.

Yamaoka et al., "Distribution and Tissue Uptake of Poly(Ethylene Glycol) with Different Molecular Weights After Intravenous Administration to Mice", *Journal of Pharmaceutical Sciences*, 83(4):601-606 (1994).

Ashraf et al., "Comperative effects of intraduodenal psyllium and senna on canine small bowel motility", *Aliment. Pharmacol. Ther.*, 8:329-336 (1994).

Bailey et al., "Invovlement of DT-diaphorase (EC 1.6.99.2) in the DNA cross-linking and sequence selectivity of the bioreductive antitumor agent E09", *Br. J. Cancer*, 76(12):1596-1603 (1997).

Begleiter et al., "Induction of DT-Diaphorase in Cancer Chemoprevention and Chemotherapy", *Oncol. Res.*, 9:371-382 (1997).

Chuang et al., "Oxidative free radical reaction of 2-phenylthio-1,4-naphthoquinones initiated by manganese(III) acetate", *Heterocylcles*, 43(10):2215-2221 (1996).

Chung et al., "Acceleration of the Alcohol Oxidation Rate in Rats with Aloin, a Quinone Derivative of Aloe", *Biochem. Pharmacol.*, 52:1461-1468 (1996).

Clarys et al., "Efficacy of Topical Treatment of Pigmentation Skin Disorders with Plant Hydroquinone Glucosides as Assessed by Quantitative Color Analysis", *J. Dermatol.*, 25:412-414 (1998).

Cortelli et al., "Clinical and brain bioenergetics improvement with idebenone in a patient with Leber's hereditary optic neuropathy: a clinical and $^{31}$P-MRS study", *J. Neurol. Sci.*, 148:25-31 (1997).

Driscoll, J.S., "Quinone Structure-Antitumor Activity Relationships", *Cancer Chemother. Reports*, 4(4):3-4 (1974).

Gantchev et al., "Inhibition of the Topoisomerase II-DNA Cleavable Complex by the ortho-Quinone Derivative of the Abtitumor Drug Etoposide (VP-16)", *Biochem. Biophys. Res. Commun.*, 237:24-27 (1997).

Goncalves et al., "Evaluation of the Toxicity of 3-allyl-β-lapachone Against *Trypanosoma cruzi* Bloodstream Forms", *Mol. Biochem. Parasitol.*, 1:167-176 (1980).

Huang et al., "β-Lapachone Induces Cell Cycle Arrest and Apoptosis in Human Colon Cancer Cells", *Mol Med*, 5:711-720 (1999).

Krapcho et al., "Heterosubstituted Anthracene-9,10-dione Analogues. The Synthesis and Antitumor Evaluation of 5,8-Bis[(aminoalkyl)amino]naphtho[2,3-*b*]thiophene-4,9-diones", *J. Med. Chem.*, 33(9):2651-2655 (1990).

Kurokawa, S., "The Reaction of Cadalene and Eudalene with Sulfur", *Bull. Chem. Soc.* Japan, 43:1454-1459 (1970).

Lai et al., "β-lapachone induced cell death in human hepatoma (HepA2) cells", *Histol Histopathol*, 13:89-97 (1998).

Li et al., "Induction of Apoptosis by β-Lapachone in Human Prostate Cancer Cells", *Cancer Res.*, 55:3712-3715 (1995).

Li et al., "β-Lapachone, a Novel DNA Topoisomerase I Inhibitor with a Mode of Action Different from Camptothecin", *J. Biol. Chem.*, 268(30):22463-22468 (1993).

Li et al., "Release of Mitochondrial Cytochrome C in Both Apoptosis and Necrosis Induced by β-Lapachone in Human Carcinoma Cells", *Mol. Med.*, 5:232-239 (1999).

Li et al., "Potent Induction of Apoptosis by β-Lapachone in Human Multiple Myeloma Cell Lines and Patient Cells", *Mol. Med.*, 6(12):1008-1015 (2000).

Li et al., "Selective killing of cancer cells by β-lapachone: Direct checkpoint activation as a strategy against cancer", *Proc. Natl. Acad. Sci. USA*, 100(5):2674-2678 (2003).

Li et al., "Potent inhibition of tumor survival in vivo by β-lapachone plus taxol: Combining drugs imposes different artificial checkpoints", *Proc. Natl. Acad. Sci. USA*, 96(23):13369-13374 (1999).

Mahadik et al., "Oxidative injury and potential use of antioxidants in schizophrenia", *Prostaglandins Leukot.. Essent. Fatty Acids*, 55(1&2):45-54 (1996).

Mordente et al., "Antioxidant Properties of 2,3-Dimethoxy-5-methyl-6(10-hydroxydecyl)-1,4-benzoquinone (Idebenone)", *Chem. Res. Toxicol.*, 11:54-63 (1998).

Muller-Lissner et al., "Adverse Effects of Laxatives: Fact and Fiction", *Pharmacol.*, 47(Suppl. 1):138-145 (1993).

Nanji et al., "Association between Endothelial Cell Proliferation and Pathologic Charges in Experimental Alcoholic Liver Disease", *Toxicol. Appl. Pharmacol.* 140:101-107 (1996).

Planchon et al., "β-Lapachone-mediated Apoptosis in Human Promyelocytic Leukemia (HL-60) and Human Prostate Cancer Cells: A p53-independent Response", *Cancer Res.*, 55:3706-3711 (1995).

Portela, et al., "Redox Cycling of β-Lapachone and Related o-Naphthoquinones in the Presence of dihydrolipoamide and Oxygen", *Biochem. Pharmacol.*, 51:275-283 (1996).

Rao et al., "A comparative study of the redox-cycling of a quinone (rifamycin S) and a quinonimine (rifabutin) antibiotic by rat liver microsomes", *Free Radic. Biol. Med.*, 22(3):439-446 (1997).

Schaffner-Sabba et al., "β-Lapachone: Synthesis of Derivatives and Activities in Tumor Models", *J. Med. Chem.*, 27:990-994 (1984).

Singh et al., "Capsaicin (8-Methyl-N-Vanillyl-6-Nonenamide) Is a Potent Inhibitor of Nuclear Transcription Factor-κB Activation by Diverse Agents", *J. Immunol.*, 157:4412-4420 (1996).

Suginome et al., "One-step Synthesis of 2,3-Dihydronaphtho[2,3-*b*]thiophene-4,9-diones by a New Regioselective [3+2] Photoaddition of Photogenerated 2-Mercapto-1,4-naphthoquinone with Alkenes[1]", *J. Chem. Soc., Chem. Commun.*, 9:807-809 (1993).

Tapia et al., "Synthesis of 2*H*-Naphtho[2,3-*b*]Thiopyranoquinones and Density Functional Study for the Diels-Alder Reaction of a Benzothiopyranoquinone", *Heterocycles*, 53(3):585-598 (2000).

Tapia et al., "Synthesis of 3,4-Dihydro-4-hydroxy-9-methoxy-2*H*-naphtho[2,3-b]thiopyranoquinone", *Tetrahedron Lett.*, 38(1):153-154 (1997).

Tonholo et al., "Electrochemical Properties of Biologically Active Heterocyclic Naphthoquinones", *J. Braz. Chem. Soc.*, 9(2):163-169 (1998).

Weller et al., "Topoisomerase-I inhibitors for human malignant glioma: differential modulation of p53, p21, bax and bcl-2 expression and of CD95-mediated apoptosis by camptothecin and β-lapachone", *Int. J. Cancer*, 73:707-714 (1997).

Wuerzberger et al., "Induction of Apoptosis in MCF-7:WS8 Breast Cancer Cells by β-Lapachone", *Cancer Res.*, 58:1876-1885 (1998).

HYDROXY SULFONATE OF QUINONE COMPOUNDS AND THEIR USES

CROSS-REFERENCE TO RELATED APPLICATIONS

This application claims the benefit of U.S. Provisional Applications No. 60/914,971, filed Apr. 30, 2007, the contents of which are incorporated herein by reference in their entirety.

FIELD OF THE INVENTION

The present invention provides sodium 6-hydroxy-2,2-dimethyl-5-oxo-3,4,5,6-tetrahydro-2H-benzo(h)chromene-6-sulfonate, and its synthesis and uses in the treatment of cancer.

BACKGROUND OF THE INVENTION

Quinones are a group of aromatic dioxo compounds derived from benzene or multiple-ring hydrocarbons such as naphthalene, anthracene, etc. They are classified as benzoquinones, naphthoquinones, anthraquinones, etc., on the basis of the ring system. Quinones are found in all major groups of organisms as a large and varied group of natural products. Quinones have a variety of medicinal and industrial uses.

Many antineoplastic drugs are either quinones (anthracycline derivatives, mitoxantrone, actinomycin), quinonoid derivatives (quinolones, genistein, bactracyclin), or drugs such as etoposide that can easily be converted to quinones by in vivo oxidation (Gantchev et al. (1997) *Biochem. Biophys. Res. Comm.* 237:24-27). Quinones are now widely used as anti-cancer, anti-bacterial and anti-malarial drugs, as well as fungicides. The antitumor activities of the quinones were revealed more than two decades ago when the National Cancer Institute published a report in which fifteen-hundred synthetic and natural quinones were screened for their anticancer activities (Driscoll et al. (1974) *Cancer Chemot. Reports* 4:1-362).

For example, β-lapachone (3,4-dihydro-2,2-dimethyl-2H-naphtho[1,2-b]pyran-5,6-dione) is a quinone derived from lapachol (a naphthoquinone). Lapachol can be isolated from the lapacho tree (*Tabebuia avellanedae*), a member of the catalpa family (Bignoniaceae). Lapachol and β-lapachone (with numbering) have the following chemical structures:

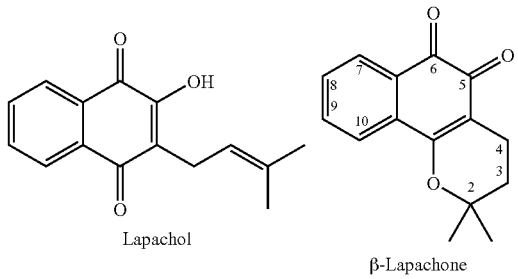

Lapachol

β-Lapachone

β-lapachone, as well as its intermediates, derivatives and analogs thereof, are described in Li, C. J. et al., (1993) *J. Biol. Chem.*, 268(30): 22463-22468. As a single agent, β-lapachone has demonstrated significant antineoplastic activity against human cancer cell lines at concentrations typically in the range of 1-10 μM ($IC_{50}$). Cytotoxicity has been demonstrated in transformed cell lines derived from patients with promyelocytic leukemia (Planchon et al., (1996) *Cancer Res.*, 55: 3706-3711), prostate (Li, C. J., et al., (1995) *Cancer Res.*, 55: 3712-3715), malignant glioma (Weller, M. et al., (1997) *Int. J. Cancer*, 73: 707-714), hepatoma (Lai, C. C., et al., (1998) *Histol Histopathol*, 13: 89-97), colon (Huang, L., et al., (1999) *Mol Med*, 5: 711-720), breast (Wuertzberger, S. M., et al., (1998) *Cancer Res.*, 58: 1876), ovarian (Li, C. J. et al., (1999) *Proc. Natl. Acad. Sci. USA*, 96(23): 13369-13374), pancreatic (Li, Y., et al., (2000) *Mol Med*, 6: 1008-1015; Li, Y., (1999) *Mol Med*, 5: 232-239), and multiple myeloma cell lines, including drug-resistant lines (Li, Y., (2000) *Mol Med*, 6: 1008-1015). No cytotoxic effects were observed on normal or proliferating human PBMC (Li, Y., (2000) *Mol Med*, 6: 1008-1015).

β-lapachone appears to work by activating DNA damage response/checkpoint pathways, which may involve unscheduled expression of checkpoint molecules, e.g. E2F1, independent of DNA damage and cell cycle stages. Several studies have shown that β-lapachone activates checkpoint pathways and induces cell death in cancer cells from a variety of tissues without causing death of normal cells from these tissues (U.S. Patent Application Publication No. 2002/0169135, incorporated by reference herein). In normal cells with their intact regulatory mechanisms, such an imposed expression of a checkpoint molecule results in a transient expression pattern and causes little consequence. In contrast, cancer and pre-cancer cells have defective mechanisms. Drug-induced elevation of checkpoint molecules, e.g. E2F1, can lead to selective cell death in these disregulated cells.

In addition to β-lapachone, a number of β-lapachone analogs having antiproliferative properties have been disclosed in the art, such as those described in PCT International Application PCT/US93/07878 (WO94/04145), which is incorporated by reference herein, and U.S. Pat. No. 6,245,807, incorporated by reference herein, in which a variety of substituents may be attached at positions 3- and 4- on the β-lapachone compound. PCT International Application PCT/US00/10169 (WO 00/61142), incorporated by reference herein, discloses β-lapachone, which may have a variety of substituents at the 3-position as well as in place of the methyl groups attached at the 2-position. U.S. Pat. Nos. 5,763,625, 5,824,700, and 5,969,163, each of which is incorporated by reference herein, disclose analogs and derivatives with a variety of substituents at the 2-, 3- and 4-positions. Furthermore, a number of journals report β-lapachone analogs and derivatives with substituents at one or more of the following positions: 2-, 3-, 8- and/or 9-positions, (See, Sabba et al., (1984) *J Med Chem* 27:990-994 (substituents at the 2-, 8- and 9-positions); (Portela and Stoppani, (1996) *Biochem Pharm* 51:275-283 (substituents at the 2- and 9-positions); Goncalves et al., (1998) *Molecular and Biochemical Parasitology* 1: 167-176 (substituents at the 2- and 3-positions)).

U.S. Patent Application Publication No. 2004/0266857 and PCT International Application PCT/US2003/037219 (WO 04/045557), incorporated by reference herein, disclose and several journal reports describe structures having sulfur-containing hetero-rings in the "α" and "β" positions of lapachone (Kurokawa S, (1970) Bulletin of *The Chemical Society of Japan* 43:1454-1459; Tapia, R A et al., (2000) *Heterocycles* 53(3):585-598; Tapia, R A et al., (1997) *Tetrahedron Letters* 38(1):153-154; Chuang, C P et al., (1996) *Heterocycles* 40(10):2215-2221; Suginome H et al., (1993) *Journal of the Chemical Society, Chemical Communications* 9:807-809; Tonholo J et al., (1988) *Journal of the Brazilian Chemical Society* 9(2): 163-169; and Krapcho A P et al., (1990) *Journal of Medicinal Chemistry* 33(9):2651-2655).

Moreover, PCT Application PCT/US06/20780, incorporated by reference herein, discloses tricyclic spiro-oxathiine naphthoquinone derivatives, a synthetic method for making the derivatives, and the use of the derivatives to induce cell death and/or to inhibit proliferation of cancer or precancerous cells. The naphthoquinone derivatives of the present invention are related to β-lapachone. WO 2006/128120, incorporated by reference herein, discloses sulfur analogs and derivatives of β-lapachone as well as methods of use thereof. These compounds can be used in pharmaceutical compositions for the treatment or prevention of cell proliferation disorders.

In addition to their antineoplastic uses, quinones also have a number of other medicinal uses. Terpenioid-type quinones are also useful as treatments for diabetes. U.S. Pat. No. 5,674, 900. Additional quinones can be used to treat cirrhosis and other liver disorders. U.S. Pat. Nos. 5,210,239 and 5,385,942.

Hydroquinone amines and quinone amines are also useful for treating a number of conditions, including spinal trauma and head injury. U.S. Pat. No. 5,120,843. Degenerative central nervous system diseases, as well as vascular diseases, are treatable with quinones such as Idebenone [2,3-dimethoxy-5-methyl-6-(10-hydroxydecyl)-1,4-benzoquinone] and Rifamycin (S. Mordente et al. (1998) *Chem. Res. Toxicol.* 11:54-63; Rao et al. (1997) *Free Radic. Biol. Med* 22:439-46; Cortelli et al. (1997)*J. Neurol. Sci.* 148:25-31; and Mahadik et al. (1996) *Prostaglandins Leukot. Essent. Fatty Acids* 55:45-54). A vitamin K analog, 6-cyclo-octylamino-5,8-quinoline quinone, shows efficacy for treatment of leprosy and tuberculosis. (U.S. Pat. No. 4,963,565). Hydroquinone is also used to treat skin pigmentation disorders. Clarys et al. (1998) *J. Dermatol.* 25:412-4. Mitomycin C-related drug indoloquinone EO9 has demonstrated cell killing against HL-60 human leukemia cells, H661 human lung cancer cells, rat Walker tumor cells and human HT29 colon carcinoma cells (Begleiter el al. (1997) *Oncol. Res.* 9:371-82; and Bailey et al. (1997) *Br. J. Cancer* 76:1596-603).

Quinones such as aloin, a C-glycoside derivative of anthraquinone, accelerate ethanol oxidation and may be useful in treating acute alcohol intoxication. (Chung et al. (1996) *Biochem. Pharmacol.* 52:1461-8 and Nanji et al. (1996) *Toxicol. Appl. Pharmacol.* 140:101-7). Quinones capsaicin and resiniferatoxin blocked activation of nuclear transcription factor NF-κB, which is required for viral replication, immune regulation and induction of various inflammatory and growth-regulatory genes (Singh et al. (1996) *J. Immunol.* 157:4412-20). Antiretroviral and antiprotozoan naphthoquinones are described in U.S. Pat. Nos. 5,780,514 and 5,783, 598. Anthraquinones are also useful as laxatives (Ashraf et al. (1994)*Aliment. Pharmacol. Ther.* 8:329-36; and Muller-Lissner (1993) *Pharmacol.* 47 (Suppl. 1): 138-45).

Because of the wide variety of biological processes in which quinones play a critical role, it would be advantageous to develop novel quinones for various uses, including disease treatment.

One obstacle, however, to the development of pharmaceutical formulations comprising quinones, such as β-lapachone or β-lapachone analogs, for pharmaceutical use is the low solubility of many quinone compounds, including β-lapachone compounds, in pharmaceutically acceptable solvents. There are also drawbacks related to the pharmacokinetic profiles of traditional formulations comprising quinones.

U.S. Pat. Nos. 6,962,944 and 7,074,824 disclose pharmaceutical compositions comprising a therapeutically effective amount of β-lapachone, or a derivative or analog thereof, and a pharmaceutically acceptable solubilizing carrier molecule, which may be a water-solubilizing carrier molecule such as hydroxypropyl-β-cyclodextrin, or an oil-based solubilizing carrier molecule, for enhancing the solubility of β-lapachone in aqueous solution. The therapeutically effective amount of β-lapachone, or a derivative or analog thereof, may be complexed with the pharmaceutically acceptable solubilizing carrier molecule in aqueous solution.

WO 2006/020719 discloses quinone prodrug compositions and therapeutic methods using such prodrug compositions. The quinone compounds of the invention are preferably naphthoquinone compounds such as β-lapachone or β-lapachone analogs. The quinone prodrug compositions exhibit improved solubility, stability, bioavailability, and pharmacokinetic properties, as well as improved plasma half-life in vivo.

There is still a need for improved formulations of quinone compounds for pharmaceutical administration, which are both safe and readily bioavailable to the subject to which the formulation is administered.

The references cited herein are not admitted to be prior art to the claimed invention.

SUMMARY OF THE INVENTION

The present invention provides a compound of formula I:

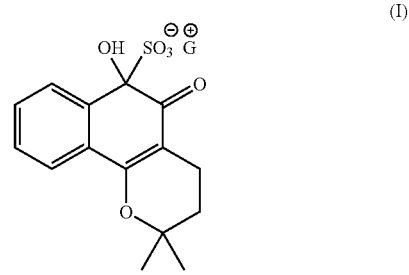

(I)

or a pharmaceutically acceptable salt and/or an individual enantiomer/diastereomer thereof, wherein G is a cation.

In an embodiment, the G is a metal cation. The metal cation can be selected from the group consisting of $H^+$, $Na^+$, $K^+$, $Li^+$, and $Ca^{2+}$. In another embodiment, the G is $N^+(R_1)_4$, wherein each $R_1$ is independently selected from the group consisting of H, $C_2$-$C_6$ straight alkyl, $C_3$-$C_6$ branched alkyl, $C_3$-$C_8$ cycloalkyl, $C_5$-$C_8$ cycloalkenyl, phenyl, $C_5$-$C_8$ aryl, and benzyl.

The purity of the compound can be 50% or more, 60% or more, 70% or more, 80% or more, 90% or more, 95% or more, or 99% or more. The compound of formula I can be in crystalline form, lyophilized form, or aqueous solution.

In an embodiment, the compound is

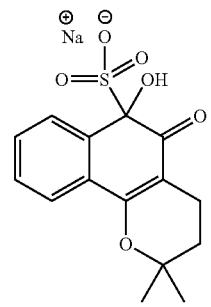

or a pharmaceutically acceptable salt and/or an individual enantiomer/diastereomer thereof.

The present invention also provides a pharmaceutical composition comprising the compound of formula I. The concentration of the compound can be in the range from 0.01 M to 0.1 M.

In an embodiment, the pharmaceutical composition further comprises a pharmaceutically acceptable solubilizing carrier molecule. The solubilizing carrier molecule can be cyclodextrin or substituted cyclodextrin. The solubilizing carrier molecule can also be β-cyclodextrin or γ-cyclodextrin. In a further embodiment, the solubilizing carrier molecule is hydroxypropyl-β-cyclodextrin (HPβCD). The concentration of HPβCD can be in the range from 1% to 20%.

The pharmaceutical composition can further comprise an antioxidant, such as sodium thiosulfate, ethylene diamine tetraacetic acid (EDTA), or Butylated hydroxytoluene (BHT). The pharmaceutical composition can also comprise polyethylene glycol (PEG) or ethanol.

The pharmaceutical composition can further comprise a buffer, such as sodium acetate buffer. The pH of the pharmaceutical composition can be from 3 to 7. In an embodiment, the pH is from 4 to 6.

The present invention also provides a pharmaceutical composition comprising β-lapachone in the form of crystalline particles wherein 90% of the particles have a diameter of 100 μm or lower, 30 μm or lower, or 10 μm or lower. The pharmaceutical composition can further comprise a particle carrier, such as lactose or mannitol. The pharmaceutical composition can further comprise a bisulfite agent. The bisulfite agent can be selected from the group consisting of metabisulfite salt such as sodium metabisulfite, bisulfite salt such as sodium bisulfite, and dithionite salt. The pharmaceutical composition can be sterilized with means known in the field, such as gamma radiation.

The present invention further provides a method of treating a cell proliferative disorder. The method comprise administering to a subject in need thereof a therapeutically effective amount of the compound of formula I, or a pharmaceutically acceptable salt thereof, or a prodrug or metabolite thereof, in combination with a pharmaceutically acceptable carrier, wherein said cell proliferative disorder is treated.

The cell proliferative disorder can be a precancerous condition or a cancer. In an embodiment, the cancer is adenocarcinoma, squamous carcinoma, sarcoma, lymphoma, multiple myeloma, or leukemia. In another embodiment, the cancer is lung cancer, colon cancer, breast cancer, pancreatic cancer, prostate cancer, acute leukemia, chronic leukemia, multiple melanoma, ovarian cancer, malignant glioma, leiomyosarcoma, hepatoma, or head and neck cancer.

The compound of claim 1, or a pharmaceutically acceptable salt thereof, or a prodrug or metabolite thereof, can be administered in combination with a second chemotherapeutic agent. In an embodiment, the second chemotherapeutic agent is selected from the group consisting of tamoxifen, raloxifene, anastrozole, exemestane, letrozole, cisplatin, carboplatin, paclitaxel, cyclophosphamide, lovastatin, minosine, gemcitabine, Cytarabine (araC), 5-fluorouracil, methotrexate, docetaxel, goserelin, vincristin, vinblastin, nocodazole, teniposide, etoposide, epothilone, navelbine, camptothecin, daunonibicin, dactinomycin, mnitoxantrone, amsacrine, doxorubicin, epirubicin, idarubicin imatanib, gefitinib, erlotinib, sorafenib, sunitinib malate, trastuzumab, rituximab, cetuximab, and bevacizumab. The cancer can be primary cancer or metastatic cancer.

In an embodiment, treating cancer comprises a reduction in tumor size, a delay of tumor growth, an improvement in the survival of patients, or an improvement in the quality of patient life.

The present invention also provides a synthetic process. The process comprises mixing a quinone compound, or a derivative or an analog thereof, and a bisulfite agent. The quinone compound can be an ortho-quinonie compound, a tetra-substituted ortho-quinone compound, or β-lapachone, or a derivative or analog thereof. As used hereini, bisulfite agent is a source of bisulfite in an aqueous solution, which is capable of producing $HSO_3^-$ in aqueous solution. The bisulfite agent can be metabisulfite salt, bisulfite salt, or dithionite salt. The present invention further provides a compound prepared by the process.

The present invention also provides a synthetic process. The process comprises mixing β-lapachone, and a bisulfite agent in an aqueous solution. In an embodiment, the bisulfite agent is selected from the group consisting of metabisulfite salt such as sodium metabisulfite, bisulfite salt such as sodium bisulfite, and dithionite salt. The pH of the aqueous solution can be 7 or lower, 6 or lower, 5 or lower, 4 or lower, or 3 or lower. The molar ratio of the bisulfite to β-lapachone can be 4 or less, 3 or less, 2 or less, or 1 or less.

The process can further comprise micronizing the β-lapachone before the step of mixing. The process can also comprise adding a particle carrier, such as lactose or mannitol, to the micronized β-lapachone before the step of mixing.

In an embodiment, the β-lapachone is in crystalline form. In a further embodiment, the β-lapachone is in the form of crystalline particles wherein 90% of the particles have a diameter of 200 pun or lower, 100 μm or lower, 30 μm or lower, or 10 μm or lower.

The process can further comprise inputting energy, such as ultrasonic energy into the aqueous solution.

The present invention also provides a kit for the treatment of a mammalian tumor. The kit comprises a first container containing a β-lapachone composition, and a second container containing a bisulfite agent.

In an embodiment, the β-lapachone composition comprising β-lapachone in the form of crystalline particles wherein 90% of the particles have a diameter of 30 μm or lower, or 10 μm or lower. The β-lapachone composition can further comprises a particle carrier, such as lactose or mannitol.

The bisulfite agent can be selected from the group consisting of metabisulfite salt such as sodium metabisulfite, bisulfite salt such as sodium bisulfite, and dithionite salt. In an embodiment, the bisulfite agent is in a solution coinmprising a buffer. The solution can further comprises an antioxidant.

In an embodiment, both the β-lapachone composition and the bisulfite agent are sterilized. The β-lapachone composition can be sterilized with gamma radiation. The bisulfite reagent can be sterilized with sterile filtration or steam sterilization.

The kit can further comprise a conduit connecting the first container and the second container. The conduit can comprise a valve.

The present invention also provides a method of improving the solubility of quinone compound comprising mixing a quinone compound, or a derivative or an analog thereof, and a chemical agent that is source of bisulfite in an aqueous solution. The quinone compound can be an ortho-quinone compound, a tetra-substituted ortho-quinone compound, β-lapachone, or a derivative or analog thereof.

Other features and advantages of the present invention are apparent from the additional descriptions provided herein including the different examples. The provided examples illustrate different components and methodology useful in practicing the present invention. The examples do not limit the claimed invention. Based on the present disclosure the skilled artisan can identify and employ other components and methodology useful for practicing the present invention.

BRIEF DESCRIPTION OF THE DRAWINGS

FIG. 1A shows the effect of sodium metabisulfite.

FIG. 1B shows the effect of sodium bisulfite.

FIG. 1C shows the effects of sodium metabisulfite, sodium bisulfite, and sodium dithionite.

DETAILED DESCRIPTION OF THE INVENTION

I. The Compounds

Figure 1A:
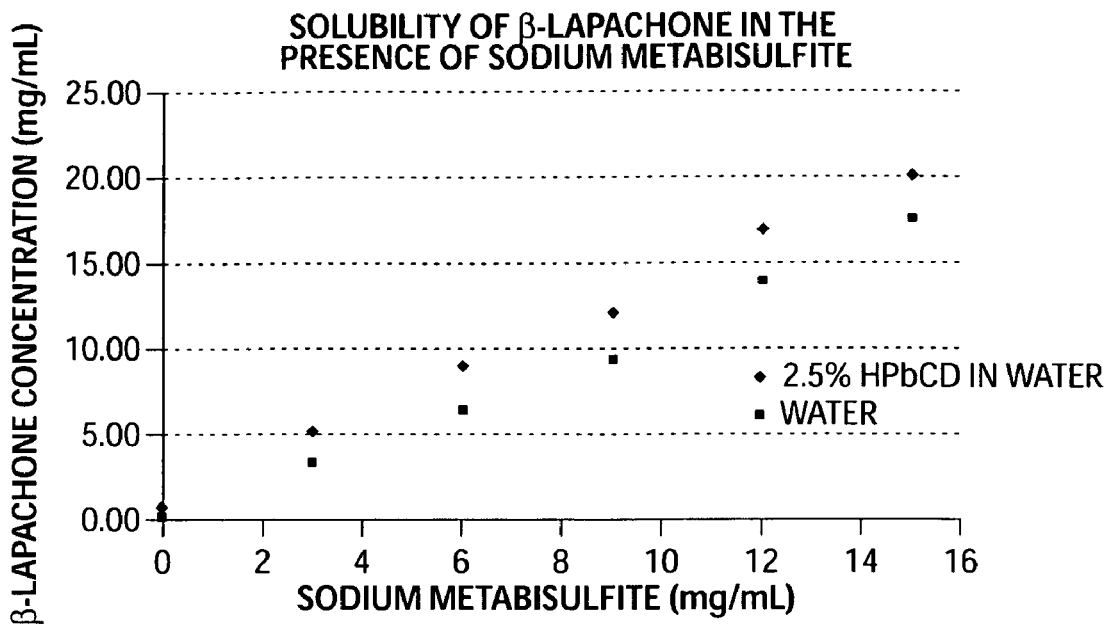
FIGS. 1A through 1C show the effect of bisulfite on the solubility of β-lapachone.

The present invention provides a compound of formula I:

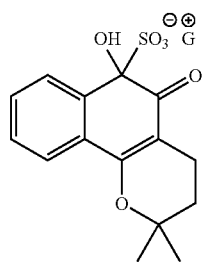

(I)

or a pharmaceutically acceptable salt and/or an individual enantiomer/diastereomer thereof, wherein G is a cation.

In an embodiment, the G can be a metal cation. In a further embodiment, the G can be selected from the group consisting of $H^+$, $Na^+$, $K^+$, $Li^+$, and $Ca^{2+}$.

Alternatively, the G can be $N^+(R_1)_4$, wherein each $R_1$ is independently selected from the group consisting of H, $C_2$-$C_6$ straight alkyl, $C_3$-$C_6$ branched alkyl, $C_3$-$C_8$ cycloalkyl, $C_5$-$C_8$ cycloalkenyl, phenyl, $C_5$-$C_8$ aryl, and benzyl.

In an embodiment, the compound of the present invention is compound 1:

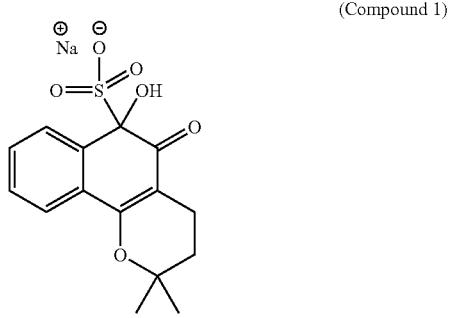

(Compound 1)

or a pharmaceutically acceptable salt and/or an individual enantiomer/diastereomer thereof.

The purity of the compound of formula I or Compound 1 can be 10% or more, 20% or more, 30% or more, 40% or more, 50% or more, 60% or more, 70% or more, 80% or more, 90% or more, 95% or more, or 99% or more. As used herein, the purity of the compound of formula I or Compound 1 refers to the percentage of the hydroxy sulfonate of β-lapachone in total β-lapachone (i.e., hydroxy sulfonate of β-lapachone and β-lapachone).

The compound of formula I or Compound 1 can be isolated as a solid in crystalline form, lyophilized form, or aqueous form. The crystalline form or lyophilized form of the compound of formula I or Compound 1 can be reconstituted.

The compound of formula I or Compound 1 can revert back to β-lapachone in certain conditions, including dilution at physiological pH, or in plasma of humans or other mammals.

II. The Synthesis of Hydroxy Sulfonate Lapachone Compound

The present invention also provides a synthetic process. The process comprises mixing a quinone compound, or a derivative or an analog thereof, and a bisulfite agent.

The quinone compound can be an ortho-quinone compound or a tetra-substituted ortho-quinone compound. In an embodiment, the quinone compound is β-lapachone, or a derivative or analog thereof. In a further embodiment, the quinone compound is β-lapachone.

The bisulfite agent is a chemical agent that is a source of bisulfite in an aqueous solution, which is capable of producing $HSO_3^-$ in aqueous solution. The bisulfite agent is capable of converting quinones to hydroxy sulfonates as in compound 1. Such a bisulfite agent can be selected from the group consisting of metabisulfite salt, bisulfite salt, and dithionite salt. Specifically, the chemical agent can be sodium metabisulfite, or sodium bisulfite. Sodium metabisulfite ($Na_2O_5S_2$, CAS #7681-57-4), sodium bisulfite ($HNaO_3S$, CAS 7631-90-5), and sodium dithionite ($Na_2S_2O_4$, CAS #7775-14-6) have been used in several FDA approved IV injectable pharmaceutical drugs.

In an embodiment, the bisulfite agent is capable of converting the quinone compound to a hydroxy sulfonate of a quinone compound. The resulting hydroxy sulfonate of the quinone compound is more soluble than the quinone compound. In certain conditions, the hydroxy sulfonate of the quinone compound can revert back to the quinone compound.

In an embodiment, the pH of the aqueous solution for the preparation of the compound of the present invention is 7 or lower, 6 or lower, 5 or lower, 4 or lower, or 3 or lower.

In an embodiment, the molar ratio of the $HSO_3^-$ to β-lapachone is 4 or less, 3 or less, 2 or less, or 1 or less.

Throughout the description, where compositions are described as having, including, or comprising specific components, it is contemplated that compositions also consist essentially of, or consist of, the recited components. Similarly, where methods or processes are described as having, including, or comprising specific process steps, the processes also consist essentially of, or consist of, the recited processing steps. Further, it should be understood that the order of steps or order for performing certain actions is immaterial so long as the invention remains operable. Moreover, two or more steps or actions can be conducted simultaneously.

The synthetic processes of the invention can tolerate a wide variety of functional groups, therefore various substituted starting materials can be used. The processes generally provide the desired final compound at or near the end of the overall process, although it may be desirable in certain instances to further convert the compound to a pharmaceutically acceptable salt, ester, or prodrug thereof.

Compounds of the invention can be prepared in a variety of ways, some of which are known in the art. In general, the compounds of the present invention can be prepared from commercially available starting materials, compounds known in the literature, or from readily-prepared intermediates, by employing standard synthetic methods and procedures known to those skilled in the art, or which will be apparent to the skilled artisan in light of the teachings herein. Standard synthetic methods and procedures for the preparation of organic molecules and functional group transformations and manipulations can be obtained from the relevant scientific literature or from standard textbooks in the field. Although not limited to any one or several sources, classic texts such as Smith, M. B.; March, J. March's Advanced Organic Chemistry: Reactions, Mechanisms, and Structure, 5$^{th}$ ed.; John Wiley & Sons: New York, 2001; and Greene, T. W.; Wuts, P. G. M. Protective Groups in Organic Synthesis, 3$^{rd}$; John Wiley & Sons: New York, 1999, incorporated by reference herein, are useful and recognized reference textbooks of organic synthesis known to those in the art. The following descriptions of synthetic methods are designed to illustrate, but not limit, general procedures for the preparation of compounds of the invention.

The compounds of this invention with general formula (I) may be prepared according to the following scheme from commercially available starting material or starting materials, which can be prepared using literature procedures. These schemes show the preparation of representative compounds of this invention.

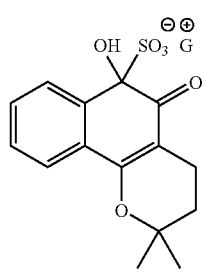

(I)

The present invention also provides methods for the synthesis of the compounds of Formula I. In one embodiment, the present invention provides a method for the synthesis of compounds according to the following schemes, and the protocols shown in the Examples.

In an embodiment, the compounds of Formula I can be prepared from the reaction of 2,2-dimethyl-2,3-dihydro-2H-benzo(h)chromene-5,6-dione (β-lapachone) and appropriate intermediate/commercial reagents. (Scheme 1)

Scheme 1

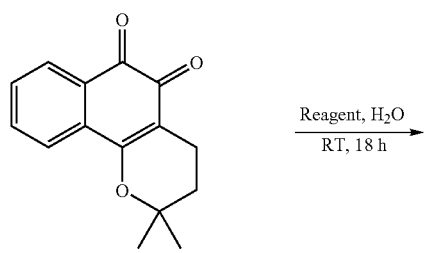

Reagent, H$_2$O
RT, 18 h

-continued

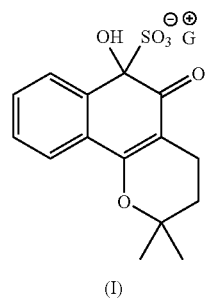

(I)

β-lapachone can be conveniently prepared by a variety of methods familiar to those skilled in the art. (see, e.g., U.S. Pat. No. 6,458,974, for the synthesis of β-lapachone). The hydroxy sulfonates (I) can be conveniently prepared by treating quinones especially ortho-quinones with reagents that are sources of nucleophilic bisulfites such as sodium metabisulfite, sodium hydrogensulfite, sodium dithionite, potassium metabisulfite including bisulfite sources with different metal and substituted and unsubstituted ammonium cations.

The particle size of β-lapachone plays an important role in the reaction rate for the formation of Compound 1. Smaller particle size of β-lapachone causes the reaction with the bisulfite to occur faster by decreasing the time needed to dissolve β-lapachone. For example when β-lapachone contains large particles (e.g., 90% less than 400-500 μm), it takes a minimum of 18 hours for the reaction to go to completion. However, when β-lapachone is micronized (e.g., 90% of the particles are below 10 μm), the conversion occurs rapidly (e.g., in about 1 minute).

The present invention provides a β-lapachone composition, which comprises β-lapachone in the form of crystalline particles with small particle size. In an embodiment, 90% of the particles have a diameter of 200 μm or lower, 100 μm or lower, 30 μm or lower, or 10 μm or lower. The β-lapachone composition can further comprise a particle carrier such as lactose or mannitol. The β-lapachone composition can by sterilized with the means such as gamma radiation.

The crystalline β-lapachone can be micronized using various means known in the field, such as air-jet milling, and ball milling. The particle size of crystalline β-lapachone can be measured using the device known in the field such as laser diffraction detector, e.g., Mastersizer 2000 (Malvern Instruments). See, e.g., Kippax & Park, *Measuring particle size using modern laser diffraction techniques.*

The conversion rate also depends on the amount of energy used for the mixing. When high energy (e.g., ultrasonic energy) is used, the conversion is complete within several minutes regardless of the particle size.

The hydroxy sulfonate (I) can be isolated as a crystalline solid, a lyophilized solid, or as a solution. The hydroxy sulfonate (I) obtained as a lyophilized powder can be dissolved in water, DMSO, acetonitrile/water mixtures (1:1 to 1:3), etc.

III. The Pharmaceutical Compositions and Formulations

The present invention provides a pharmaceutical composition comprising the compound of the present invention such as the compound of formula I or compound 1. In an embodiment, the concentration of the compound of the present invention is in the range from 0.0001 M to 0.2 M, 0.001 M to 0.1 M, 0.01 M to 0.1 M, 0.02 M to 0.09 M, 0.03 M to 0.08M, 0.04 M to 0.07 M, or 0.05 M to 0.06 M.

The pharmaceutical composition can be provided to the end user in a number of forms.

In an embodiment, the pharmaceutical composition is a sterile solution, which is further diluted with an acceptable fluid for intravenous administration. The pharmaceutical composition can comprise a combination of antioxidants and co-solvents. The pharmaceutical composition can further comprise a dextrose solution or a combination of dextrose and a buffer such as sodium acetate buffer, for the purpose of intravenous administration. The pH of the pharmaceutical composition can be from 3 to 6. In an embodiment, the pH is 5.

The antioxidant can be such as sodium thiosulfate, ethylene diamine tetraacetic acid (EDTA), or Butylated hydroxytoluene (BHT).

The pharmaceutical composition of the present invention can further comprise a pharmaceutically acceptable solubilizing carrier molecule. The solubilizing carrier molecule can be cyclodextrin or substituted cyclodextrin. The solubilizing carrier molecule can also be β-cyclodextrin, γ-cyclodextrin or (x-cyclodextrin. In an embodiment, the solubilizing carrier molecule is HPβCD. In a further embodiment, the concentration of HPβCD is in the range from 0.1% to 20%, 0.5% to 10%, 1% to 6%, or 2% to 5%.

The pharmaceutical composition can also comprise polyethylene glycol (PEG) or ethanol or both.

In another embodiment, the pharmaceutical composition is in solid form, which can be dissolved with water or a buffer. The pharmaceutical composition comprises β-lapachone in the form of crystalline particles wherein 90% of the particles have a diameter of 30 μm or lower, or 10 μm or lower, and a bisulfite agent. The bisulfite agent can be selected from the group consisting of metabisulfite salt such as sodium metabisulfite, bisulfite salt such as sodium bisulfite, and dithionite salt. The pharmaceutical composition can further comprise a particle carrier such as lactose or mannitol. Alternatively, the particle carrier can be the bisulfite agent. The pharmaceutical composition can by sterilized with the means such as gamma radiation.

In an alternative embodiment, the product could be a kit containing two independent primary containers such as vials. In this case the two respective vials would contain: (1) β-lapachone as a micronized or milled solid mixed with suitable excipients and (2) a solution containing a reagent (that is a source of bisulfite) in a buffer. β-lapachone could be terminally sterilized by gamma radiation or other means of sterilization. The bisulfite solution could be terminally sterilized by sterile filtration or steam sterilization. Compound 1 is prepared prior to administration by adding the bisulfite solution to the vial containing β-lapachone and mixing for several minutes until β-lapachone completely dissolves and is converted by the source of bisulfite to compound 1.

The present invention provides a kit for the treatment of a mammalian tumor. The kit comprises a first container containing a β-lapachone composition, and a second container containing a bisulfite agent.

In an embodiment, the β-lapachone composition comprises β-lapachone in the form of crystalline particles wherein 90% of the particles have a diameter of 30 μm or lower, or 10 μm or lower. The β-lapachone composition can further comprise a particle carrier, such as lactose particle or mannitol particle.

In an embodiment, the bisulfite agent is selected from the group consisting of metabisulfite salt such as sodium metabisulfite, bisulfite salt such as sodium bisulfite, and dithionite salt. In an embodiment, the bisulfite agent is in a solution comprising a buffer. The solution can further comprise an antioxidant.

Both the β-lapachone composition and the bisulfite agent can be sterilized. The β-lapachone composition can be sterilized with gamma radiation. The bisulfite reagent in solution can be sterilized with sterile filtration or steam sterilization.

In an embodiment, the kit further comprises a conduit connecting the first container and the second container. The conduit can comprise a valve.

The kit may comprise instructions how to make compound 1 by mixing the β-lapachone composition and the bisulfite agent, how to administer the compound 1.

A "pharmaceutically acceptable salt" or "salt" of the disclosed compound is a product of the disclosed compound that contains an ionic bond, and is typically produced by reacting the disclosed compound with either an acid or a base, suitable for administering to a subject. Pharmaceutically acceptable salt can include, but is not limited to, acid addition salts including hydrochlorides, hydrobromides, phosphates, sulphates, hydrogen sulphates, alkylsulphonates, arylsulphonates, acetates, benzoates, citrates, maleates, fumarates, succinates, lactates, and tartrates; alkali metal cations such as Na, K, Li, alkali earth metal salts such as Mg or Ca, or organic amine salts.

A "pharmaceutical composition" is a formulation containing the disclosed compounds in a form suitable for administration to a subject.

In one embodiment, the pharmaceutical composition is in bulk or in unit dosage form. The unit dosage form is any of a variety of forms, including, for example, a capsule, an TV bag, a tablet, a single pump on an aerosol inhaler, or a vial. The quantity of active ingredient (e.g., a formulation of the disclosed compound or salts thereof) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including oral, pulmonary, rectal, parenteral, transdermal, subcutaneous, intravenous, intramuscular, intraperitoneal, intranasal, and the like. Dosage forms for the topical or transdermal administration of a compound of this invention include powders, sprays, ointments, pastes, creams, lotions, gels, solutions, patches and inhalants. In one embodiment, the active compound is mixed under sterile conditions with a pharmaceutically acceptable carrier, and with any preservatives, buffers, or propellants that are required.

The present invention also provides pharmaceutical formulations comprising a compound of Formula I in combination with at least one pharmaceutically acceptable excipient or carrier. As used herein, "pharmaceutically acceptable excipient" or "pharmaceutically acceptable carrier" is intended to include any and all solvents, dispersion media, coatings, antibacterial and antifungal agents, isotonic and absorption delaying agents, and the like, compatible with pharmaceutical administration. Suitable carriers are described in "Remington: The Science and Practice of Pharmacy, Twentieth Edition," Lippincott Williams & Wilkins, Philadelphia, Pa., which is incorporated herein by reference. Examples of such carriers or diluents include, but are not limited to, water, saline, Ringer's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

Methods for formulation are disclosed in PCT International Application PCT/US02/24262 (WO03/011224), U.S. Patent Application Publication No. 2003/0091639 and U.S. Patent Application Publication No. 2004/0071775, each of which is incorporated by reference herein.

A compound of Formula I is administered in a suitable dosage form prepared by combining a therapeutically effective amount (e.g., an efficacious level sufficient to achieve the desired therapeutic effect through inhibition of tumor growth, killing of tumor cells, treatment or prevention of cell proliferative disorders, etc.) of a compound of Formula I (as an active ingredient) with standard pharmaceutical carriers or diluents according to conventional procedures (i.e., by producing a pharmaceutical composition of the invention). These procedures may involve mixing, granulating, and compressing or dissolving the ingredients as appropriate to attain the desired preparation. In another embodiment, a therapeutically effective amount of a compound of Formula I is administered in a suitable dosage form without standard pharmaceutical carriers or diluents.

Pharmaceutically acceptable carriers include solid carriers such as lactose, terra alba, sucrose, talc, gelatin, agar, pectin, acacia, magnesium stearate, stearic acid and the like. Exemplary liquid carriers include syrup, peanut oil, olive oil, water and the like. Similarly, the carrier or diluent may include time-delay material known in the art, such as glyceryl monostearate or glyceryl distearate, alone or with a wax, ethylcellulose, hydroxypropylmethylcellulose, methylmethacrylate or the like. Other fillers, excipients, flavorants, and other additives such as are known in the art may also be included in a pharmaceutical composition according to this invention.

The pharmaceutical compositions containing active compounds of the present invention may be manufactured in a manner that is generally known, e.g., by means of conventional mixing, dissolving, granulating, dragee-making, levigating, emulsifying, encapsulating, entrapping, or lyophilizing processes. Pharmaceutical compositions may be formulated in a conventional manner using one or more physiologically acceptable carriers comprising excipients and/or auxiliaries which facilitate processing of the active compounds into preparations that can be used pharmaceutically. Of course, the appropriate formulation is dependent upon the route of administration chosen.

A compound or pharmaceutical composition of the invention can be administered to a subject in many of the well-known methods currently used for chemotherapeutic treatment. For example, for treatment of cancers, a compound of the invention may be injected directly into tumors, injected into the blood stream or body cavities or taken orally or applied through the skin with patches. For treatment of psoriatic conditions, systemic administration (e.g., oral administration), or topical administration to affected areas of the skin, are preferred routes of administration. The dose chosen should be sufficient to constitute effective treatment but not so high as to cause unacceptable side effects. The state of the disease condition (e.g., cancer, psoriasis, and the like) and the health of the patient should be closely monitored during and for a reasonable period after treatment.

IV. Methods of Treatment

As described above, under certain conditions, such as mixing with human plasma, the compounds of formula I can convert back to β-lapachone, which has significant antineoplastic activity against various human cancer cells.

The present invention also provides a method for the treatment of a cell proliferative disorder in a mammal comprising administering to a mammal in need of such treatment, a therapeutically effective amount of a compound of the present invention such as a compound of Formula I. The invention further provides the use of a compound of Formula I for the preparation of a medicament useful for the treatment of a cell proliferative disorder. In one embodiment, the invention provides for the treatment of cancer or precancerous conditions in a mammal comprising administering to a mammal in need of such treatment, a therapeutically effective amount of a compound of Formula I. The mammal can be e.g., any mammal, e.g., a human, a primate, mouse, rat, dog, cat, cow, horse, pig. For example, the mammal is a human.

An effective amount of a compound of Formula I is used in a method to treat a cell proliferative disorder in a mammal without affecting normal cells of the mammal. For example, a therapeutically effective amount of a compound of Formula I is used in a method for treating cancer in a mammal by inducing cell death in cancer cells without affecting normal cells in the mammal. Cell death can occur by either apoptosis or necrosis mechanisms. In another example, administration of a therapeutically effective amount of a compound of Formula I induces sustained (non-transient) activity (e.g. elevation of the level) of a checkpoint molecule in abnormally proliferating cells without affecting checkpoint molecule activity in normal cells. For example, administration of a therapeutically effective amount of a compound of Formula I induces activation of E2F1 checkpoint pathway in abnormally proliferating cells without significantly affecting normal cells. In another example, administration induces sustained E2F pathway activity (e.g. elevation of E2F levels) in cancer cells without affecting E2F pathway activity (e.g. E2F levels) in normal cells. Methods of measuring induction of E2F activity and elevation of E2F levels are as shown in Li el al., (2003) *Proc Natl Acad Sci USA*. 100(5): 2674-8. In another example, administration of a therapeutically effective amount of a compound of Formula I induces cell death in abnormally proliferating cells without inducing cell death in normal cells.

The invention also provides a method of protecting against a cell proliferative disorder in a mammal by administering a therapeutically effective amount of a compound of Formula I to a mammal. The invention also provides the use of a compound of Formula I for the preparation of a medicament useful for the prevention of a cell proliferative disorder. In one embodiment, the invention provides for the prevention of cancer in a mammal comprising administering to a mammal in need of such treatment, a therapeutically effective amount of a compound of Formula I.

The compounds of the invention are administered in the form of pharmaceutical compositions, e.g., as described herein.

As used herein, a "subject" can be any mammal, e.g., a human, a primate, mouse, rat, dog, cat, cow, horse, pig, sheep, goat, camel. In a preferred aspect, the subject is a human.

As used herein, a "subject in need thereof" is a subject having a cell proliferative disorder, or a subject having an increased risk of developing a cell proliferative disorder relative to the population at large. In one aspect, a subject in need thereof has a precancerous condition. In a preferred aspect, a subject in need thereof has cancer.

As used herein, the term "cell proliferative disorder" refers to conditions in which the unregulated and/or abnormal growth of cells can lead to the development of an unwanted condition or disease, which can be cancerous or non-cancerous, for example a psoriatic condition. As used herein, the term "psoriatic condition" refers to disorders involving keratinocyte hyperproliferation, inflammatory cell infiltration, and cytokine alteration.

In one embodiment, the cell proliferation disorder is cancer. As used herein, the term "cancer" includes solid tumors, such as lung, breast, colon, ovarian, prostate, malignant melanoma, non-melanoma skin cancers, as well as hematologic tumors and/or malignancies, such as childhood leukemia and lymphomas, multiple myeloma, Hodgkin's disease, lymphomas of lymphocytic and cutaneous origin, acute and chronic leukemia such as acute lymphoblastic, acute myelocytic or chronic myelocytic leukemia, plasma cell neoplasm, lymphoid neoplasm and cancers associated with AIDS.

In addition to psoriatic conditions, the types of proliferative diseases which may be treated using the compositions of the present invention are epidermic and dermoid cysts, lipomas, adenomas, capillary and cutaneous hemangiomas, lymphangiomas, nevi lesions, teratomas, nephromas, myofibromatosis, osteoplastic tumors, and other dysplastic masses and the like. In one embodiment, proliferative diseases include dysplasias and disorders of the like.

As used herein, "monotherapy" refers to administration of a single active or therapeutic compound to a subject in need thereof. Preferably, monotherapy will involve administration of a therapeutically effective amount of an active compound. For example, cancer monotherapy with one of the compounds of the present invention, or a pharmaceutically acceptable salt, prodrug, metabolite, analog or derivative thereof, to a subject in need of treatment of cancer. Monotherapy may be contrasted with combination therapy, in which a combination of multiple active compounds is administered, preferably with each component of the combination present in a therapeutically effective amount. In one aspect, montherapy with a compound of the present invention is more effective than combination therapy in inducing a desired biological effect.

As used herein, "treating" describes the management and care of a patient for the purpose of combating a disease, condition, or disorder and includes the administration of a compound of the present invention to alleviate the symptoms or complications, or eliminate the disease, condition or disorder. As used herein, "preventing" describes the administration of a compound of the present invention to prevent the onset of the symptoms or complications of a disease, condition, or disorder.

In one aspect, treating cancer results in a reduction in the size of a tumor. In another aspect, treating cancer results in a reduction in tumor volume. In another aspect, treating cancer results in a decrease in number of tumors. In another aspect, treating cancer results in a decrease in number of metastatic lesions in other tissues or organs distant from the primary tumor site. In another aspect, treating cancer results in an increase in average survival time of a population of treated subjects in comparison to a population receiving carrier alone. In another aspect, treating cancer results in an increase in average survival time of a population of treated subjects in comparison to a population of untreated subjects. In another aspect, treating cancer results in an increase in average survival time of a population of treated subjects in comparison to a population receiving monotherapy with a drug that is not a compound of the present invention, or a pharmaceutically acceptable salt, prodrug, metabolite, analog or derivative thereof. In another aspect, treating cancer results in a decrease in the mortality rate of a population of treated subjects in comparison to a population receiving carrier alone. In another aspect, treating cancer results in a decrease in the mortality rate of a population of treated subjects in comparison to an untreated population. In a further aspect, treating cancer results in a decrease in the mortality rate of a population of treated subjects in comparison to a population receiving monotherapy with a drug that is not a compound of the present invention, or a pharmaceutically acceptable salt, prodrug, metabolite, analog or derivative thereof. In another aspect, treating cancer results in a decrease in tumor growth rate. In another aspect, treating cancer results in a decrease in tumor regrowth.

In another aspect, treating or preventing a cell proliferative disorder results in a reduction in the rate of cellular proliferation. In another aspect, treating or preventing a cell proliferative disorder results in a reduction in the proportion of proliferating cells. In another aspect, treating or preventing a cell proliferative disorder results in a decrease in the size of an area or zone of cellular proliferation. In another aspect, treating or preventing a cell proliferative disorder results in a decrease in the number or proportion of cells having an abnormal appearance or morphology.

In additional aspects, a compound of the present invention, or a pharmaceutically acceptable salt, metabolite, analog or derivative thereof, can be administered in combination with a chemotherapeutic agent. Exemplary chemotherapeutics with activity against cell proliferative disorders are known to those of ordinary skill in the art, and may be found in reference texts such as the *Physician's Desk Reference*, $59^{th}$ Edition, Thomson PDR (2005). For example, the chemotherapeutic agent can be a taxane, an aromatase inhibitor, an anthracycline, a microtubule targeting drug, a topoisomnerase poison drug, a targeted monoclonal or polyclonal antibody, an inhibitor of a molecular target or enzyme (e.g., a kinase inhibitor), or a cytidine analogue drug. In preferred aspects, the chemotherapeutic agent can be, but is not restricted to, tamoxifen, raloxifene, anastrozole, exemestane, letrozole, cisplatin, carboplatin, TAXOL® (paclitaxel), cyclophosphamide, lovastatin, minosine, GEMZAR® (gemcitabine HCl), cytarabine (araC), 5-fluorouracil (5-FU), methotrexate (MTX), TAXOTERE® (docetaxel), ZOLADEX® (goserelin), vincristin, vinblastin, nocodazole, teniposide, etoposide, epothilone, navelbine, camptothecin, daunonibicin, dactinomycin, mitoxantrone, amsacrine, doxorubicin (adriamycin), epirubicin, idarubicin, or GLEEVEC® (imatanib), IRESSA® (gefitinib), TARCEVA® (erlotinib), NEXAVAR® (sorafenib), SUTENT® (sunitinib malate), HERCEPTIN® (trastuzumab), RITUXAN® (Rituximab), ERBITUX® (cetuximab), AVASTIN® (bevacizumab), or agents well known in the art. In another aspect, the chemotherapeutic agent can be a cytokine such as G-CSF (granulocyte colony stimulating factor). In another aspect, β-lapachone, or a pharmaceutically acceptable salt, metabolite, analog or derivative thereof may be administered in combination with radiation therapy. In yet another aspect, β-lapachone, or a pharmaceutically acceptable salt, metabolite, analog or derivative thereof may be administered in combination with standard chemotherapy combinations such as, but not restricted to, CMF (cyclophosphamide, methotrexate and 5-fluorouracil), CAF (cyclophosphamide, adriamycin and 5-fluorouracil), AC (adriamycin and cyclophosphamide), FEC (5-fluorouracil, epirubicin, and cyclophosphamide), ACT or ATC (adriamycin, cyclophosphamide, and paclitaxel), or CMFP (cyclophosphamide, methotrexate, 5-fluorouracil and prednisone). More examples of chemotherapeutic agents can be found in WO/2004/006849.

EXAMPLES

Examples are provided below to further illustrate different features of the present invention. The examples also illustrate useful methodology for practicing the invention. These examples do not limit the claimed invention.

Example 1

Bisulfite Improves The Solubility of β-Lapachone in Aqueous Solution

Solutions of bisulfites at different concentrations were prepared in water or 2.5% HPβCD and an excess amount of β-lapachone was added to obtain a saturated solution. These solutions were shaken for 24 hours, filtered through a 0.45 μm filter, and analyzed for β-lapachone concentration by HPLC.

Figure 1B:
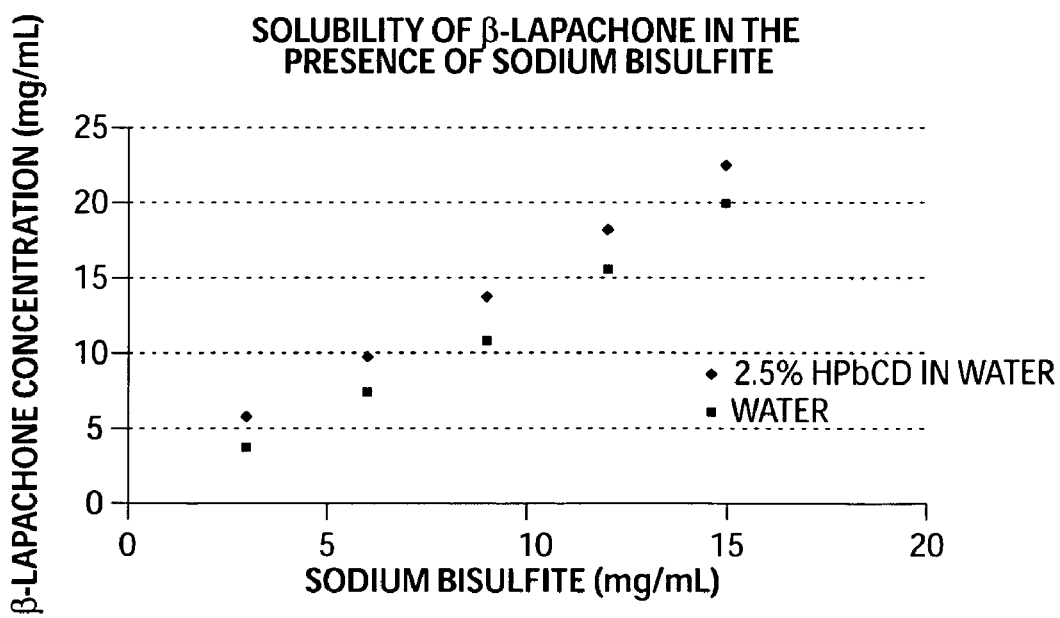
Figure 1C:
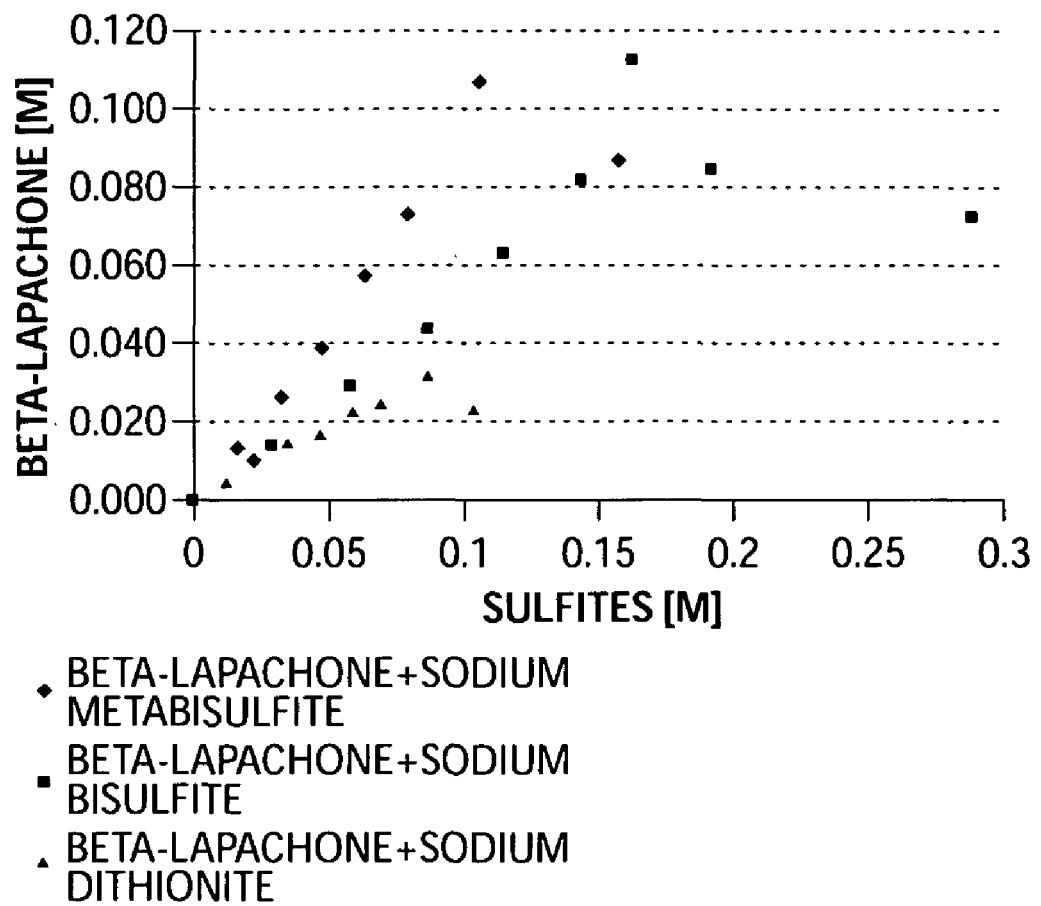

The equilibrium solubility results, in the presence and absence of HPβCD, are illustrated in FIGS. 1A to 1C. Bisulfite can enhance the equilibrium solubility of β-lapachone depending on the concentration of the bisulfites. Saturated solutions of β-lapachone with 3, 6, 9, 12 and 15 mg/mL sodium metabisulfite or sodium bisulfite were prepared in water or in 2.5-5% hydroxypropyl cyclodextrin. The solubility of the β-lapachone is directly proportional with the amounts of bisulfites added, until they reach respective saturation concentrations (See FIG. 1C). The data show that bisulfites dramatically improve the solubility of β-lapachone in aqueous solution.

Example 2

Sodium Metabisulfite Converts β-Lapachone to Sodium 6-hydroxy-2,2-dimethyl-5-oxo-3,4,5,6-tetrahydro-2H-benzo(h)chromene-6-sulfonate NMR, FT-IR, and UV-vis spectrophotometry indicate the formation of a new species, and LC-MS analysis confirms the presence of the hydroxy sulfonate of β-lapachone.

Figure 2A:
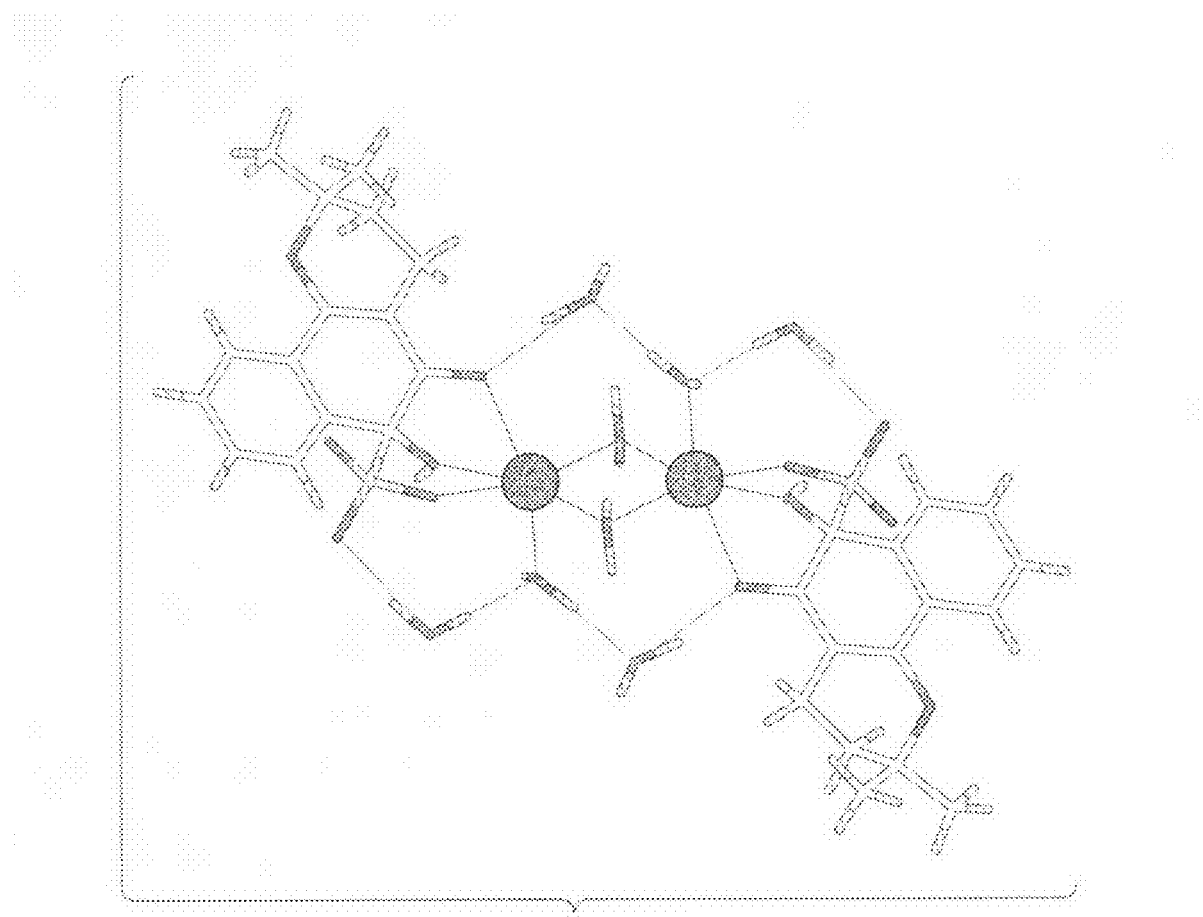
FIG. 2A shows a unit cell from the X-ray structure of 6-hydroxy-2,2-dimethyl-5-oxo-3,4,5,6-tetrahydro-2H-benzo(h)chromene-6-sulfonate.
Figure 2B:
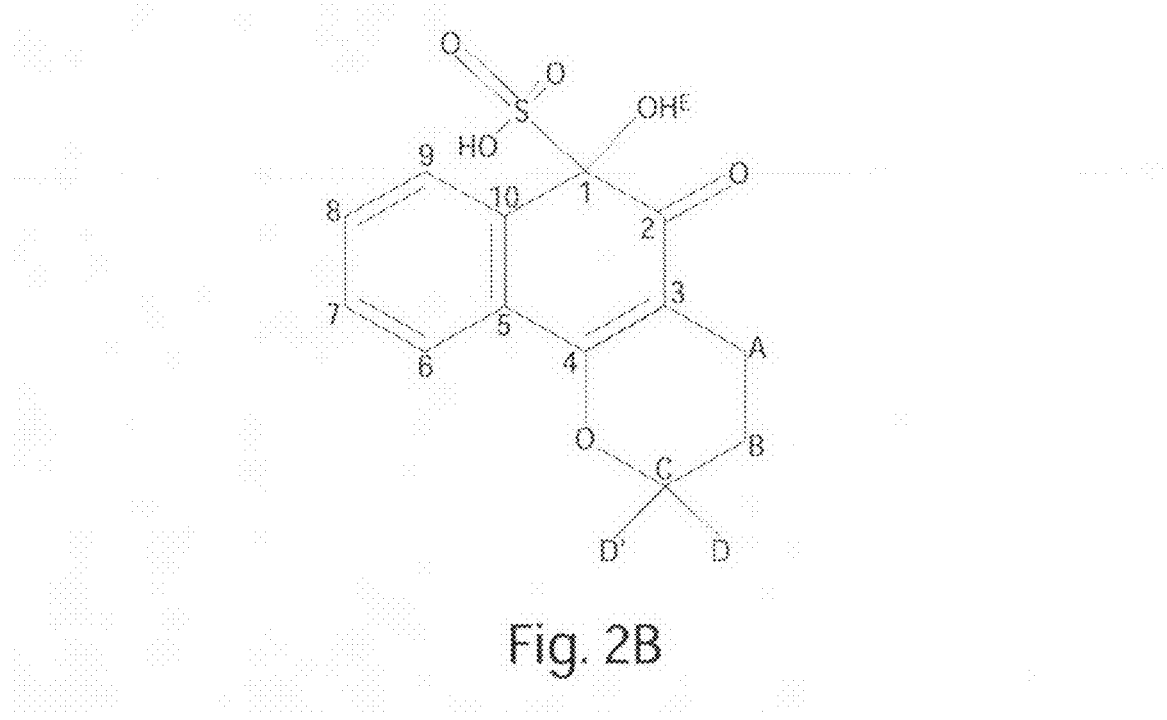
FIG. 2B shows the structure of sodium 6-hydroxy-2,2-dimethyl-5-oxo-3,4,5,6-tetrahydro-2H-benzo(h)chromene-6-sulfonate (I) with atoms labeled.

The crystalline form of the new compound has been isolated and analyzed by single crystal XRD, which confirms the presence of the 6-hydroxy-2,2-dimethyl-5-oxo-3,4,5,6-tetrahydro-2H-benzo(h)chromene-6-sulfonate as a sodium salt (see FIGS. 2A and 2B).

Example 3

The Reversion of the Compound 1 to β-Lapachone

Under certain conditions, compound 1, sodium 6-hydroxy-2,2-dimethyl-5-oxo-3,4,5,6-tetrahydro-2H-benzo(h)chromene-6-sulfonate, reverts back to β-lapachone.

Despite the results of NMR, FT-IR, and UV-vis spectrophotometry, and LC-MS, HPLC analysis of the formulation shows that the only species present is β-lapachone even though the color of the formulation becomes lighter depending on the amount of bisulfites added. The results indicate that compound 1 reverts back to β-lapachone under the conditions of sample preparation for HPLC analysis.

Studies of these formulations using UV-vis spectrophotometry show that dilution to 20-100 μM concentrations or less, or increasing the pH to 6-7 or higher, in combination with dilution converts Compound 1 back to β-lapachone. Also in diluted human plasma at pH 7, the only species present is β-lapachone. Thus, compound 1 also reverts back to β-lapachone under the conditions of high pH or when mixed with plasma.

Example 4

Preparation of Sodium 6-hydroxy-2,2-dimethyl-5-oxo-3,4,5,6-tetrahydro-2H-benzo(h)chromene-6-sulfonate with sodium metabisulfite sodium bisulfites, and sodium dithionite The compound can be prepared at different concentrations (0.01-0.1 M) depending on the amount of sodium metabisulfite, sodium bisulfite or sodium dithionite added. (See FIG. 1C) Solutions of bisulfites (sodium metabisulfite, sodium bisulfite and sodium dithionite) at different concentrations were prepared in water, acetate buffer or lactate buffer or 2.5% HPβCD or the combination of those and the appropriate amount of amount of β-lapachone was added to obtain a 10-20 mg/mL concentration. These solutions were shaken for 18-24 hours and filtered through a 0.45 μm filter. The same formulation was prepared as a lyophilized solid with the addition of 2.5-5% mannitol as a bulking agent.

1. β-lapachone with $Na_2S_2O_5$ or $NaHSO_3$ in acetate buffer 600 mg of β-lapachone was added to 40 mL of 40 mM sodium acetate buffer at pH 5 containing 15 mg/mL $Na_2S_2O_5$ or $NaHSO_3$. The solution was mixed for 22.5 hours at room temperature, and filtered through a 0.45 μm PVDF filter.

2. β-lapachone with $Na_2S_2O_5$ or $NaHSO_3$ in 5% HP β-CD 600 mg of β-lapachone was added to 40 mL of 5% (wt/vol) HP β-CD (hydroxypropyl beta-cyclodextrin) containing 15 mg/mL $Na_2S_2O_5$ or $NaHSO_3$. The solution was mixed for 22.5 hours at room temperature and filtered through a 0.45 μm PVDF filter.

3. Lyophilized β-lapachone with $Na_2S_2O_5$ 750 mg of β-lapachone was added to 50 mL of an aqueous solution containing 20 mg/mL $Na_2S_2O_5$ and 5% mannaitol. The solution was mixed for 18 hours at room temperature, and filtered through a 0.45 μm PVDF filter and lyophilized. The lyophilized solid can be reconstituted with water or 5% dextrose.

Example 5

Synthesis of Sodium 6-hydroxy-2,2-dimethyl-5-oxo-3,4,5,6-tetrahydro-2H-benzo(h)chromene-6-sulfonate (Compound 1)

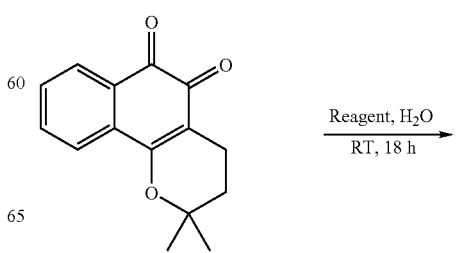

-continued

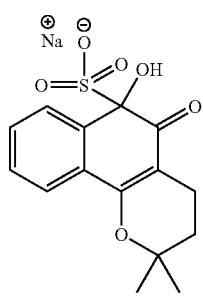

Reagent: Na$_2$S$_2$O$_5$, Na$_2$S$_2$O$_4$, or NaHSO$_3$

Procedure A:

To an aqueous solution (100 mL) of sodium metabisulfite (2.01 g, 10.5 mmol) was added 2,2-dimethyl-2,3-dihydro-2H-benzo(h)chromene-5,6-dione (1.503 g, 6.2 mmol). The reaction mixture was stirred at room temperature for 18 hours and then stored at 4° C. for 72 hours. Yellow crystals of the desired product separated out. The supernatant was filtered, and the isolated crystals were dried. The crystals were subjected to single crystal X-ray diffraction. The results are shown in FIG. 2A. In the crystal lattice, Compound 1 is present as a dimer with two sodium molecules and 8 molecules of water.

Alternatively, to a 124-310 mM solution of sodium metabisulfite or potassium metabisulfite (20 mL), 0.15M sodium chloride and 0.04M potassium chloride was added. The reaction mixture was stirred at room temperature for 1-10 hours, at which point the desired product crystallized out. The crystals were maintained as a suspension in the reaction mixture. The crystals could also be isolated by filtration.

Procedure B:

To a solution of 2,2-dimethyl-2,3-dihydro-2H-benzo(h)chromene-5,6-dione (0.217 g, 0.9 mmol) in acetonitrile (5 mL) was added an aqueous solution (5 mL) of sodium metabisulfite (0.34 g, 1.8 mmol). The reaction mixture was mixed and lyophilized. The desired product was obtained as a yellowish orange solid. LCMS: m/z=323 (ESI-). 1D and 2D NMR [300 MHz $^1$H NMR (DMSO-d$_6$), 75 MHz $^{13}$C NMR (DMSO-d$_6$)] see Table A and B, FIG. 2B.

TABLE A $^1$H Chemical shifts of sodium 6-hydroxy-2,2-dimethyl-5-oxo-3,4,5,6-tetrahydro-2H-benzo(h)chromene-6-sulfonate (I) in DMSO-d$_6$ solvent

| | Procedure B | | |
|---|---|---|---|
| SITE | ppm | Multiplicity (J) | # of protons |
| 1 | — | — | — |
| 2 | — | — | — |
| 3 | — | — | — |
| 4 | — | — | — |
| 5 | — | — | — |
| 6 | 7.6 | m | 1H |
| 7 | 7.34 | m | 1H |
| 8 | 7.34 | m | 1H |
| 9 | 7.65 | m | 1H |
| 10 | | | |
| A | 2.36, 2.48 | m | 1H, 1H |
| B | 1.66, 1.81 | m | 1H, 1H |
| C | | | |
| D, D' | 1.34, 1.39 | s | 3H, 3H |
| E | 5.87 | s | 1H |
| | | exchangable | |

TABLE B $^{13}$C Chemical shifts of sodium 6-hydroxy-2,2-dimethyl-5-oxo-3,4,5,6-tetrahydro-2H-benzo(h)chromene-6-sulfonate (I) and $^1$H—$^{13}$C HMBC connectivities in DMSO-d$_6$ solvent

| | Procedure B | | HMBC connectivities | |
|---|---|---|---|---|
| SITE | ppm | type of Carbon | ppm (H site) | |
| 1 | 90.70 | Q | 5.87 (E) | 7.65 (9) |
| 2 | 196.18 | Q | 5.87 (E) | 2.36, 2.48 (A) |
| 3 | 108.47 | Q | 2.36, 2.48 (A) | 1.66, 1.81 (B) |
| 4 | 161.53 | Q | 2.36, 2.48 (A) | 7.6 (6) |
| 5 | 129.14 | Q | 7.34 (7) | |
| 6 | 122.36 | CH | 7.34 (8) | |
| 7 | 127.80 | CH | 7.65 (9) | |
| 8 | 128.91 | CH | 7.6 (6) | |
| 9 | 128.54 | CH | 7.34 (7) | |
| 10 | 137.97 | Q | 7.6 (6) | 7.34 (8) |
| A | 16.76 | CH2 | 1.66, 1.81 (B) | |
| B | 31.89 | CH2 | 2.36, 2.48 (A) | 1.34, 1.39 (D, D') |
| C | 78.01 | Q | 2.36, 2.48 (A) | 1.66, 1.81 (B) | 1.34, 1.39 (D, D') |
| D, D' | 25.99, 27.89 | CH3 | 1.34, 1.39 (D, D') | |
| E | — | OH | | |

Procedure C:

To an aqueous solution (3 mL) of sodium metabisulfite (0.045 g, 0.21 mmol) was added 2,2-dimethyl-2,3-dihydro-2H-benzo(h)chromene-5,6-dione (0.045 g, 0.19 mmol). The reaction mixture was stirred at room temperature for 18 hours and filtered. The desired product was formed and stored as an aqueous solution. For NMR studies, the reaction was carried out in $D_2O$. LCMS: m/z=323 (ESI-). 1D NMR: [300 MHz $^1$H NMR ($D_2O$); 75 MHz $^{13}$C NMR ($D_2O$)] see Table C and D; FIG. 2B.

Procedure D:

To an aqueous solution (5 mL) of sodium bisulfite (0.1012 g, 0.97 mmol) was added 2,2-dimethyl-2,3-dihydro-2H-benzo(h)chromene-5,6-dione (0.1031 g, 0.43 mmol). The reaction mixture was stirred at room temperature until all 2,2-dimethyl-2,3-dihydro-2H-benzo(h)chromene-5,6-dione had dissolved. The reaction mixture was lyophilized and the desired product was obtained as a yellowish orange solid. LCMS: m/z=323 (ESI-).

Procedure E:

To an aqueous solution (5 mL) of sodium bisulfite (0.019 g, 0.018 mmol) was added 2,2-dimethyl-2,3-dihydro-2H-benzo(h)chromene-5,6-dione (0.0424 g, 0.18 mmol). The reaction mixture was stirred at room temperature for 18 hours and filtered. The desired product was formed and stored as an aqueous solution. For NMR studies, the reaction was carried out in $D_2O$. LCMS: m/z=323 (ESI-). 1D NMR: [300 MHz $^1$H NMR ($D_2O$); 75 MHz $^{13}$C NMR ($D_2O$)] see Table C and D; FIG. 2B.

Procedure F:

To an aqueous solution (3 mL) of sodium dithionite (0.116 g, 0.67 mmol) was added 2,2-dimethyl-2,3-dihydro-2H-benzo(h)chromene-5,6-dione (0.0349 g, 0.14 mmol). The reaction mixture was stirred at room temperature for 18 hours and filtered. The desired product was formed and stored as an aqueous solution. For NMR studies, the reaction was carried out in $D_2O$. LCMS: m/z=323 (ESI-). 1D NMR: [300 MHz $^1$H NMR ($D_2O$); 75 MHz $^{13}$C NMR ($D_2O$)] see Table C and D; FIG. 2B.

TABLE C $^1$H chemical shifts of sodium 6-hydroxy-2,2-dimethyl-5-oxo-3,4,5,6-tetrahydro-2H-benzo(h)chromene-6-sulfonate (I) in 100% $D_2O$ solvent

| SITE | Procedure C ppm | Procedure E ppm | Procedure F ppm | Multiplicity (J) | # of protons |
|------|------|------|------|---|---|
| 1 | — | — | — | — | — |
| 2 | — | — | — | — | — |
| 3 | — | — | — | — | — |
| 4 | — | — | — | — | — |
| 5 | — | — | — | — | — |
| 6 | 7.71 | 7.64 | 7.7 | m | 1H |
| 7 | 7.37 | 7.33 | 7.36 | m | 1H |
| 8 | 7.37 | 7.33 | 7.36 | m | 1H |
| 9 | 7.59 | 7.57 | 7.59 | m | 1H |
| 10 | — | — | — | | |
| A | 2.21, 2.38 | 2.19, 2.35 | 2.20, 2.38 | m | 1H, 1H |
| B | 1.63, 1.79 | 1.57, 1.76 | 1.62, 1.79 | m | 1H, 1H |
| C | — | — | — | | |
| D, D' | 1.27, 1.33 | 1.24, 1.31 | 1.27, 1.33 | s | 3H, 3H |

TABLE D $^{13}$C chemical shifts of sodium 6-hydroxy-2,2-dimethyl-5-oxo-3,4,5,6-tetrahydro-2H-benzo(h)chromene-6-sulfonate (I) in 100% $D_2O$ solvent

| SITE | Type of Carbon | Procedure C ppm | Procedure E ppm | Procedure F ppm |
|------|------|------|------|------|
| 1 | Q | 91.72 | 91.75 | 91.70 |
| 2 | Q | 195.62 | 195.57 | 195.68 |
| 3 | Q | 109.31 | 109.28 | 109.34 |
| 4 | Q | 165.96 | 165.97 | 165.96 |
| 5 | Q | 129.58 | 129.55 | 129.60 |
| 6 | CH | 124.49 | 124.48 | 124.51 |
| 7 | CH | 130.24 | 130.24 | 130.25 |
| 8 | CH | 131.11 | 131.11 | 131.11 |
| 9 | CH | 127.66 | 127.64 | 127.66 |
| 10 | Q | 135.02 | 135.00 | 135.05 |
| A | CH2 | 16.90 | 16.90 | 16.90 |
| B | CH2 | 31.87 | 31.88 | 31.85 |
| C | Q | 80.78 | 80.77 | 80.80 |
| D, D' | CH3 | 25.64, 27.73 | 25.59, 27.82 | 25.66, 27.67 |

Example 6

Reversion of the Hydroxy Sulfonate of β-Lapachone to β-Lapachone

The hydroxy sulfonate of β-lapachone easily reverts back to β-lapachone in dilute solutions of bisulfite and other reagents. For example when a solution of Compound 1 is diluted with a mobile phase containing acetonitrile and phosphate buffer at pH 6.8 and analyzed by HPLC, only the β-lapachone can be detected. However, the mass by LC/MS for Compound 1 can be obtained using a short LC method where the acetonitrile/water mobile phase is acidified with 0.1% formic acid. Even under these conditions, two peaks are observed, one peak corresponding to Compound 1, and one to the β-lapachone released from the complex.

Figure 3:
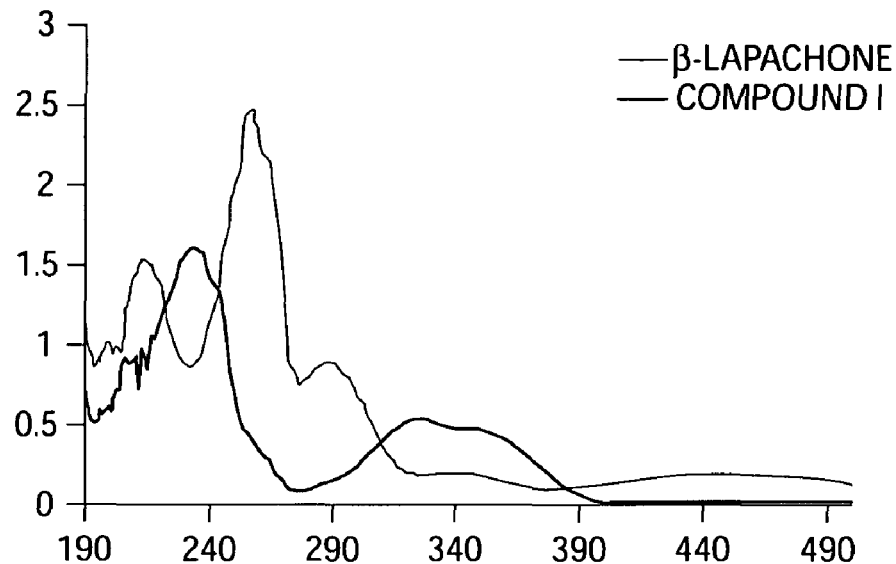
FIG. 3 shows overlay of the UV-vis spectra of the β-lapachone and hydroxy sulfonate of β-lapachone.

The UV-vis spectra of β-lapachone solutions in water and HPβCD exhibit an absorbance maximum at 256 nm and one smaller absorbance band at 213 nm. The UV absorbance maxima for Compound 1 are shifted to 233 nm and 327 nm. (See FIG. 3).

When a solution of Compound 1 is diluted in phosphate buffered saline at pH 7 or human plasma, the UV-vis spectrum become identical to that for a solution of β-lapachone.

The pH dependence of the conversion of Compound 1 to β-lapachone is demonstrated by the fact that the maximum concentrations of β-lapachone that can be converted to Compound 1 decrease with increasing pH as presented in Table E.

TABLE E

Maximum concentrations of β-lapachone converted at different pHs.

| Sulfite Agents | Sulfite Conc. (mg/mL) | Converted β-lapachone Conc. (mg/mL) | pH of the formulation |
|------|------|------|------|
| $Na_2S_2O_5$ | 5 | 5.90 | 3.01 |
| $Na_2S_2O_5$ | 5 | 5.76 | 4.46 |
| $Na_2S_2O_5$ | 5 | 1.88 | 7.04 |
| $NaHSO_3$ | 5 | 5.76 | 3.29 |
| $NaHSO_3$ | 5 | 5.97 | 4.52 |
| $NaHSO_3$ | 5 | 2.23 | 7.04 |

*appropriate amount of NaCl was added to maintain a constant ionic strength

Example 7

The Effects of Sodium Bisulfite and Sodium Metabisulfite on the Solubility of Derivatives or Analogs of β-Lapachone The solubility of eight derivatives or analogs of β-lapachone disclosed in PCT/US06/20780 was evaluated in the presence of sodium metabisulfite or sodium bisulfite with and without HPβCD. All the compounds showed an increase in solubility accompanied by a color change in the presence of the sodium metabisulfite. There is an increase of 5 to 348 times in solubility for respective compounds with sodium metabisulfite (10 mg/mL) compared to the solution without sodium metabisulfite, and 6 to 1448 times increase in solubility with sodium metabisulfite and HPβCD (5%).

Example 8

The Effect of MeβCD on the Solubility of β-Lapachone

Figure 4:
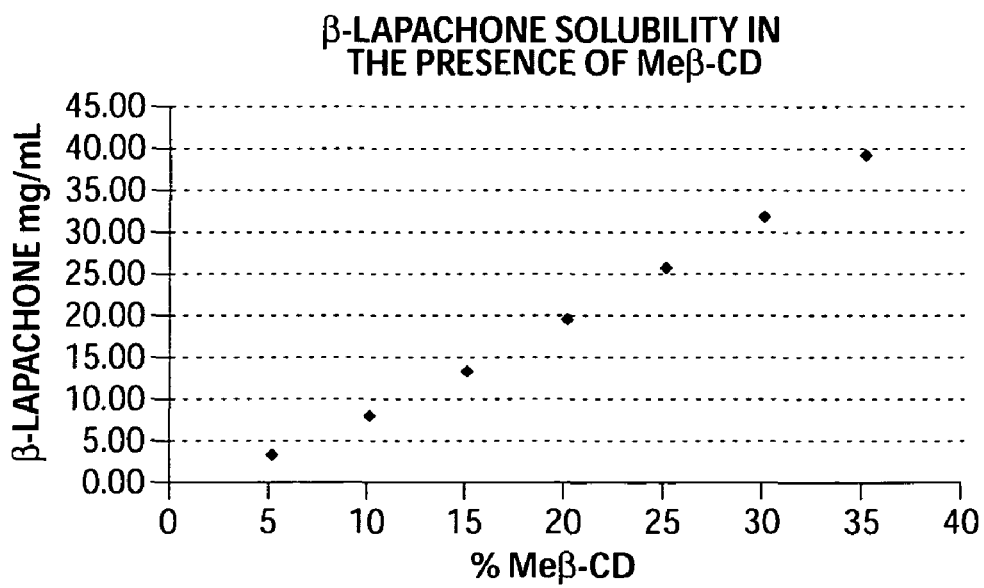
FIG. 4 shows the effect of methyl β cyclodextrin (MeβCD) on the solubility of β-lapachone.

Methyl beta-cyclodextrin (MeβCD) is a derivative of beta-cyclodextrin with 1-7 methyl substituents on the secondary O-2 positions. The solubility of β-lapachone is significantly enhanced in the presence of MeβCD. The equilibrium solubility is directly proportional to the amount of MeβCD as illustrated in FIG. 4.

The average degree of substitution (DS) has an influence on the complexing abilities of the cyclodextrin derivatives. Cyclodextrin derivatives with low DS are better solubilizing agents than cyclodextrins with high DS. HPβCD with two different degrees of substitutions, 6.9 and 4.3, were compared in terms of β-lapachone solubility. It was found that the lower degree of substitution had about a 16-17% higher solubilizing effect than the HPβCD with 6.9 DS.

Example 9

A Solution Formulation of Compound 1

Compound 1 was made under the conditions as follows:

| Component | Concentration |
|---|---|
| β-lapachone | 16.0 mg/mL |
| Sodium Metabisulfite | 16.0 mg/mL |
| Hydroxypropyl beta-cyclodextrin | 5% w/v or 50 mg/mL |
| Polyethylene glycol 300 | 10% v/v or 0.1 mL/mL |
| Sodium thiosulfate | 0.1% or 1 mg/mL |
| Sodium acetate buffer, pH 5 | 100 mM |

The pH of the formulated product with sodium acetate buffer is 5. The pH of the mixture of β-lapachone and sodium metabisulfite or sodium bisulfite is 3.

The particle size of the milled β-lapachone was measured by laser diffraction technique using a Mastersizer 2000 (Malvern Instruments). The Dv (0.9) of the milled material is in the range of 140-150 μm.

Other embodiments are within the following claims. While several embodiments have been shown and described, various modifications may be made without departing from the spirit and scope of the present invention.

What is claimed is:

1. A compound of formula I:

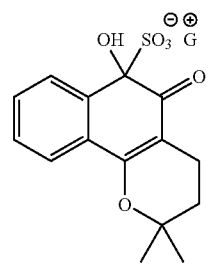

or a pharmaceutically acceptable salt and/or an individual enantiomer/diastereomer thereof; wherein G is a cation.

2. The compound of claim 1 wherein the G is selected from the group consisting of $H^+$, $Na^+$, $K^+$, $Li^+$, and $Ca^{2+}$.

3. The compound of claim 1 wherein the compound is

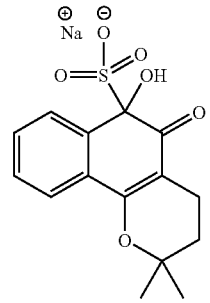

or a pharmaceutically acceptable salt and/or an individual enantiomer/diastereomer thereof.

4. The compound of claim 1 wherein the purity of the compound is 50% or more, 60% or more, 70% or more, 80% or more, 90% or more, 95% or more, or 99% or more.

5. The compound of claim 1, wherein the compound is in crystalline form, lyophilized form, or aqueous solution.

6. A pharmaceutical composition comprising the compound of claim 1.

7. The pharmaceutical composition of claim 6 wherein the concentration of the compound is in the range from 0.01 M to 0.1 M.

8. The pharmaceutical composition of claim 6 further comprising a pharmaceutically acceptable solubilizing carrier molecule.

9. The pharmaceutical composition of claim 8 wherein said solubilizing carrier molecule is hydroxypropyl-β-cyclodextrin (HPβCD).

10. The pharmaceutical composition of claim 9 wherein the concentration of HPβCD is in the range from 1% to 20%.

11. The pharmaceutical composition of claim 6 further comprising an antioxidant.

12. The pharmaceutical composition of claim 11 wherein the antioxidant is selected from the group consisting of sodium thiosulfate, ethylene diamine tetraacetic acid (EDTA), and Butylated hydroxytoluene (BHT).

13. The pharmaceutical composition of claim 6 further comprising polyethylene glycol (PEG) or ethanol.

14. The pharmaceutical composition of claim 6 further comprising a buffer.

15. The pharmaceutical composition of claim 6 wherein the pH of the pharmaceutical composition is from 3 to 7.

16. A method of treating a cell proliferative disorder, said method comprising administering to a subject in need thereof a therapeutically effective amount of the compound of claim 1, or a pharmaceutically acceptable salt thereof, or a prodrug or metabolite thereof, in combination with a pharmaceutically acceptable carrier, wherein said cell proliferative disorder is treated.

17. A synthetic process comprising mixing β-lapachone, and a bisulfate agent in an aqueous solution.

18. The process of claim 17 wherein the β-lapachone is in the form of crystalline particles wherein 90% of the particles have a diameter of 200 μm or lower, 100 μm or lower, 30 μm or lower, or 10 μm or lower.

* * * * *